United States Patent [19]
Carney et al.

[11] Patent Number: 5,604,107
[45] Date of Patent: Feb. 18, 1997

[54] DETECTION OF NEU P185 IN CELL LYSATES

[75] Inventors: Walter P. Carney, North Andover; Sara J. McKenzie, Lynn; Robert A. Weinberg, Brookline, all of Mass.

[73] Assignee: Oncogene Science, Inc., Uniondale, N.Y.

[21] Appl. No.: 220,962

[22] Filed: Mar. 30, 1994

Related U.S. Application Data

[63] Continuation of Ser. No. 2,994, Jan. 11, 1993, abandoned, which is a continuation of Ser. No. 806,112, Dec. 12, 1991, Pat. No. 5,401,638, which is a continuation of Ser. No. 412,668, Sep. 29, 1989, abandoned, which is a continuation-in-part of Ser. No. 297,188, Jan. 13, 1989, abandoned, which is a continuation-in-part of Ser. No. 182,501, Apr. 18, 1988, abandoned, which is a continuation-in-part of Ser. No. 871,102, Jun. 4, 1986, Pat. No. 4,935,341.

[51] Int. Cl.$^6$ ......................... G01N 33/574; G01N 33/53
[52] U.S. Cl. ......................... 435/7.23; 435/7.1; 435/7.7; 435/7.92; 436/64; 436/813; 530/388.8; 530/388.85
[58] Field of Search ................................. 435/7.23, 7.1, 435/7.7, 7.92; 436/64, 813; 530/388.8, 388.85

[56] References Cited

PUBLICATIONS

McKenzie, S. J., et al., *Oncogene*, 4,543–548, 1989.
*Practice & Theory of Enzyme Immunoassays*, P. Tijssen, Elsevier Science Pubs., Amsterdam, The Netherlands, 340–343, 1985.
Carney, et al., *Journal of Tumor Marker Oncology*, vol. 6, No. 2, pp. 53–72, 1991.
Gullick, et al., *Int. J. Cancer*, vol. 40, pp. 246–254, 1987.
Berger, et al, *Cancer Res.*, vol. 48, pp. 1238–1243, Mar. 1, 1988.

*Primary Examiner*—Toni R. Scheiner
*Attorney, Agent, or Firm*—John P. White

[57] ABSTRACT

This invention relates to a substantially purified p100 which is a human neu related protein having a molecular weight in the range from about 97,000 daltons to about 115,000 daltons which corresponds substantially to the extracellular domain of the human neu gene product, said protein being detectable in a biological fluid.

In another embodiment this invention relates to assays for detecting this protein.

Finally, this invention also concerns monoclonal antibodies which are capable of binding to p100.

38 Claims, 18 Drawing Sheets

FIGURE 4A
FIGURE 4B
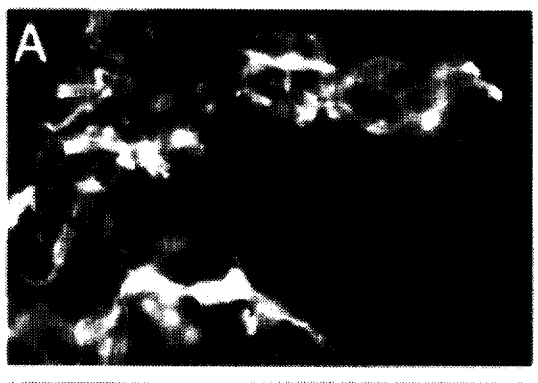
FIGURE 4C
FIGURE 4D
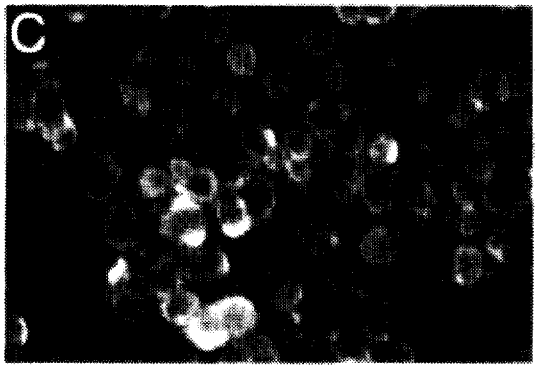
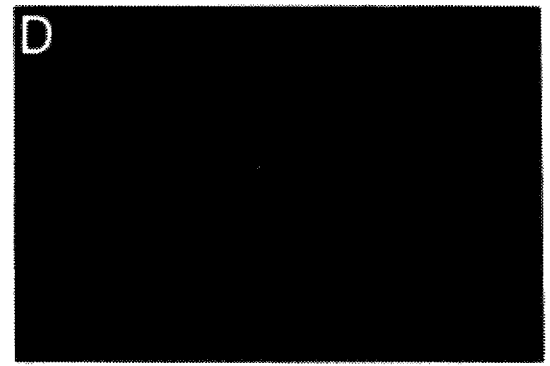

DETECTION OF NEU P185 IN CELL LYSATES

RELATED APPLICATIONS

This application is a continuation of U.S. Ser. No. 08/002, 994, filed Jan. 11, 1993, abandoned which is a continuation of U.S. Ser. No. 806,112 filed Dec. 12, 1991, now U.S. Pat. No. 5,401,638, which is a continuation of U.S. Ser. No. 412,668 filed Sep. 29, 1989, now abandoned, which was a continuation-in-part of U.S. Ser. No. 297,188 filed Jan. 13, 1989, now abandoned, which was a continuation-in-part of U.S. Ser. No. 182,501 filed Apr. 18, 1988, now abandoned, which was a continuation-in-part of U.S. Ser. No. 871,102 filed Jun. 4, 1986, now U.S. Pat. No. 4,935,341 issued Jan. 19, 1990. The teachings of the above-referenced patent are incorporated herein by reference.

FIELD OF THE INVENTION

This invention relates to a substantially purified human neu gene related product, p100, and, more particularly, to detection and/or quantification of p100 in the biological fluids of humans using monoclonal antibodies which are capable of binding to this protein.

BACKGROUND OF THE INVENTION

Rat neuro/glioblastomas induced by transplacental injection of ethylnitrosourea carry an oncogene that is detectable by transfection into mouse NIH 3T3 cells. (Shih et al., Nature (London) 290: 261–264 (1981), Schubert et al., Nature (London) 249: 224–227 (1974)). This gene was designated neu. (Schechter et al., Nature (London) 312: 513–516 (1984)). It was found that the neu gene was related to, but distinct from, the gene that encoded the epidermal growth factor receptor (EGFR). The transfected NIH 3T3 cells displayed a novel 185,000 dalton tumor antigen (p185) that was not. detected when the recipient cells were transformed by other oncogenes. (Padhy et al., Cell 28: 865–871 (1982)).

The human homolog of the rat neu oncogene has been isolated and termed c-erbB-2 or HER-2 on the basis of its close relationship to the human EGF receptor gene (also known as the c-erbB-1 gene). (Yamamoto et al., Nature 319: 230–234 (1986), Coussens et al., Science 230: 1132–1139 (1985)). The human neu protein has been reported to have a slightly higher apparent molecular weight of about 190,000 daltons. (Gullick et al., Int. J. Cancer 40: 246–254 (1987)). The DNA sequences of the rat and human clones which have been isolated predict a 1260 amino acid protein product of the neu gene that is colinear and about 50% identical with the predicted amino acid sequence of the EGF receptor. The level of sequence homology of the extracellular domains of the human EGFR and the c-erbB-2 is about 43%.

HER-2/neu differs from EGFR in that it is found on band q21 of chromosome 17 whereas the EGFR gene is located of band p11-p13 of chromosome 7. The HER-2/neu gene generates a messenger RNA (mRNA) of 4.8 kb which differs from the 5.8–10 kb transcripts for the EGFR gene. Finally, the protein encoded by the HER-2/neu gene has been found to have a molecular weight in the range from about 185,000 daltons to about 190,000 as compared to the 170,000 dalton protein encoded by the EGFR gene.

By analogy to the EGFR, the neu gene product appears to be a transmembrane protein consisting of a cysteine-rich extracellular region of about 650 amino acids, a transmembrane domain, and an intracellular portion of about 580 amino acids consisting in part of a tyrosine kinase domain.

Biochemical studies have revealed that the p185 protein is glycosylated and accessible to antisera in intact cells, consistent with its localization at the cell surface. p185 appears to be the receptor for an as yet unidentified ligand.

While a single point mutation occurring in the transmembrane domain of the protein converting a valine residue to glutamic acid was responsible for activation of the rat neu oncogene, no such mutation has been found to occur in the human neu gene. It is statistically unlikely that such a mutation would occur in the human homolog because two adjacent nucleotide changes would be needed to generate the same mutation in the transmembrane domain of the human neu gene. However, when the double mutation is induced in the human homolog, oncogenic activity is induced. This does not preclude the possibility that other point mutations could activate the human homolog.

The oncogenic potential of the human neu gene can be achieved by a mechanism other than a point mutation. Unlike the rat neu gene which is non-transforming at any level of expression unless mutated, the human neu gene is transforming, in the absence of any mutation, when overexpressed. Alteration of control of expression can be accomplished by increased expression of the pre-existing gene or by increasing the number of copies of the gene (gene amplification). Gene amplification of c-erbB-2 has been identified in primary mammary adenocarcinomas as well as in a salivary gland adenocarcinoma. Researchers have found that the human neu gene is amplified relatively frequently in human breast cancer cell lines. neu was amplified 2 to greater than 20 times in 30% of breast tumors. The presence of neu amplification was a significant predictor of both overall survival time and time relapse. (Slamon et al., Science 235: 177–182 (Jan. 9, 1987)). Thus, these findings suggest the possibility that neu overexpression, whether due to amplification or to some other mechanism, contributes to neoplastic growth.

Because the human neu protein appears to be involved in human malignancy, researchers have tried to study its expression and structure in human tissues.

Berger et al., Cancer Research 48: 1238–1243 (1988), tried to correlate c-erbB-2 gene amplification and protein expression with lymph node status and nuclear grading as well as with axillary lymph node involvement. c-erbB-2 specific antibodies generated from a synthetic peptide corresponding to residues 1215–1255 of the c-erbB-2 open reading frame were used to analyze fifty one primary human breast tumors for amplification of the c-erbB-2 proto-oncogene.

Drebin et al., Nature 312: 545–548 (1984) describe the generation of monoclonal antibodies that react specifically with cell-surface determinants found on NIH 3T3 cells transformed by transfection with a group of rat neuroblastoma oncogenes (the rat neu oncogene).

Drebin et al., Cell 41:695–706 (July 1985), describe the rapid and reversible loss of both cell-surface and total cellular p185 of NIH 3T3 cells transformed with the rat neu oncogene which were exposed to monoclonal antibodies reactive with the rat neu gene product.

Drebin et al., Oncogene 2: 273–277 (1988) describe monoclonal antibodies reactive with distinct domains of the rat neu oncogene-encoded p185 molecule which exert synergistic anti-tumor effects in vivo.

Drebin et al., Oncogene 2: 387–394 (1988), describe monoclonal antibodies which bind cell surface domains of the rat neu gene encoded product.

Expression of the c-erbB-2 protein in normal and transformed cells was investigated by Gullick et al., Int. J. Cancer 40: 246–254 (1987) using antisera generated against two synthetic peptides from the predicted sequence of the human c-erbB-2 protein and a monoclonal antibody specific for the rat neu protein.

Similarly, Venter et al., The Lancet, ii, pages 69–72 (Jul. 11, 1987) describe amplification of the human proto-oncogene c-erbB-2 in 12 of 36 human breast tumors which was associated with increased levels of expression of the c-erbB-2 protein, measured by immunohistological staining and by Western blotting. Affinity-purified rabbit antibodies, raised to a peptide consisting of residues 1215–1225 of the open reading frame of the c-erbB-2 protein, were used in the immunohistological staining.

Tandon et al., Journal of Clinical Oncology, pages 1120–1128, Vol. 7, No. 8 (August 1989), describe a method using Western blot analysis to quantitate the HER-2/neu protein levels in 728 human breast tumor specimens for the potential prognostic significance. Rabbit polyclonal antiserum was generated against the carboxy terminal synthetic peptide of the HER-2/neu protein (residues GTPTAENPEYLGLDVPV from the deduced amino acid sequence) for use in the study.

Akiyama et al., Science, pages 1644–1646, Vol. 232 (Jun. 27, 1986), also described raising antibodies against a synthetic peptide corresponding to 14 amino acid residues at the carboxy terminus of the deduced amino acid sequence from the human c-erbB-2 nucleotide sequence. The antibodies were reported to immunoprecipitate a 185,000 dalton glycoprotein from MKN-7 adenocarcinoma cells.

Most recently, regulation of the tyrosine kinase activity of the epidermal growth factor receptor by a truncated receptor of 100 kilodaltons containing the EGF-binding site but not the kinase domain was reported by Basu et al. in Molecular and Cellular Biology, pages 671–677 (February 1989). It was described that structurally related receptor kinases, such as the platelet-derived growth factor receptor, the insulin receptor, and the neu receptor, were not inhibited by the truncated 100 kDa receptor.

SUMMARY OF THE INVENTION

This invention relates to a substantially purified p100 which is a human neu related protein having a molecular weight in the range from about 97,000 daltons to about 115,000 daltons which corresponds substantially to the extracellular domain of the human neu gene product, said protein being detectable in a biological fluid.

In another embodiment this invention relates to assays for detecting this protein.

Finally, this invention also concerns monoclonal antibodies which are capable of binding to p100.

BRIEF DESCRIPTION OF THE FIGURES

FIGS. 4A, 4B, 4C and 4D presents immunofluorescent results.

STATEMENT OF DEPOSIT

Figure 1:
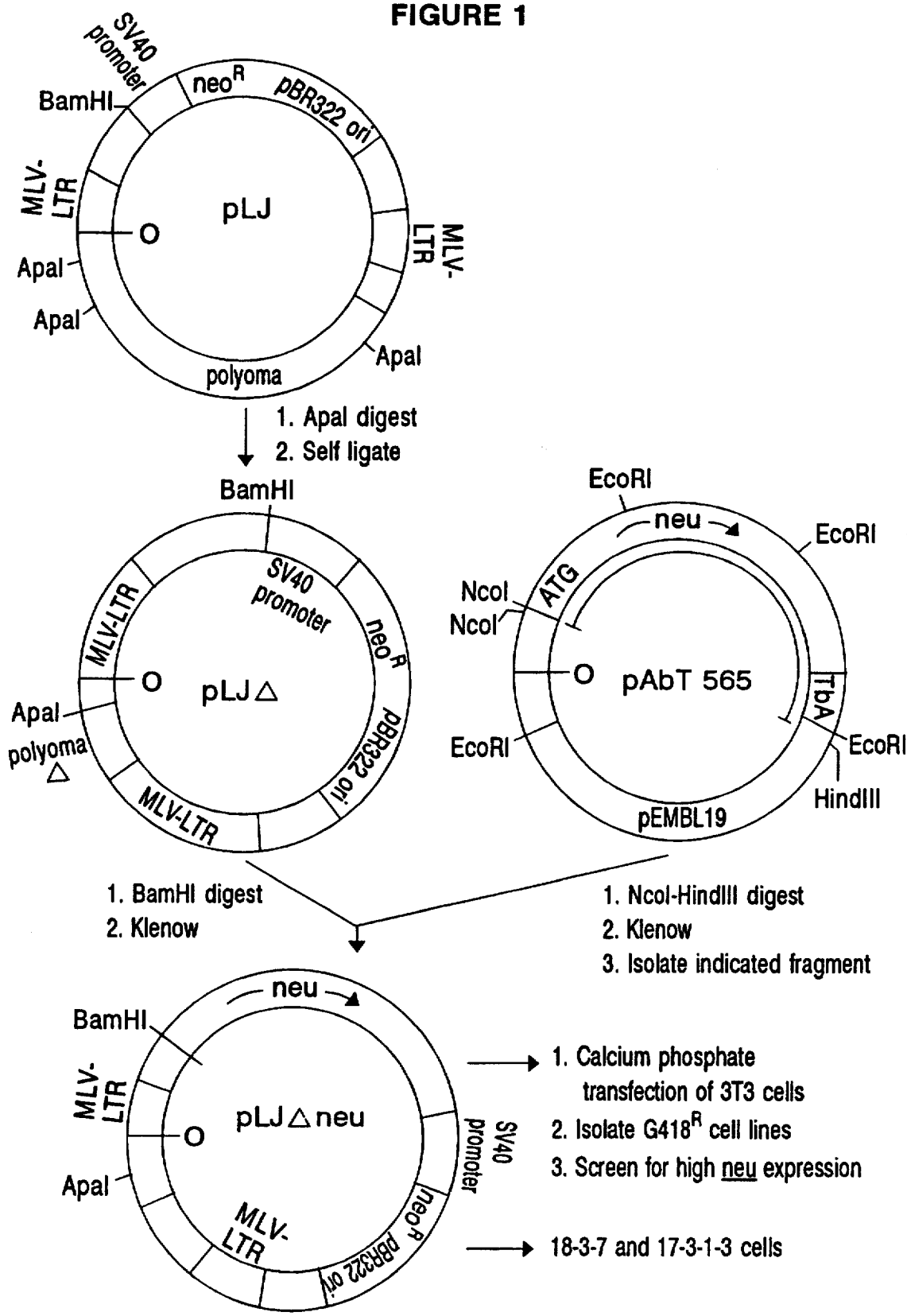
FIG. 1 is a schematic representation of plasmid vector pLJdelta neu, created by inserting the human neu gene cDNA indicated onto the pLJdelta expression vector.
Figure 2A:
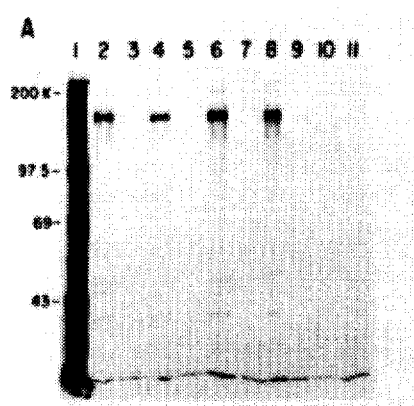
FIGS. 2A, 2B, 2C and 2D presents immunoprecipitation results indicating that the monoclonal antibodies described herein recognized a human neu related protein.
Figure 2B:
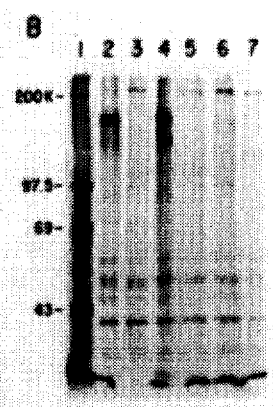
Figure 2C:
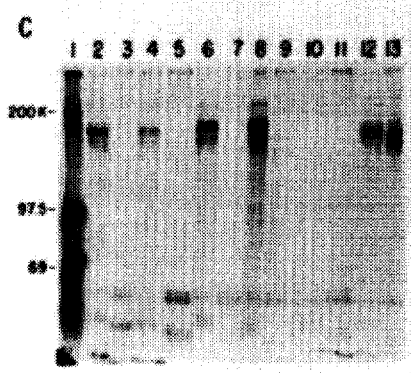
Figure 2D:
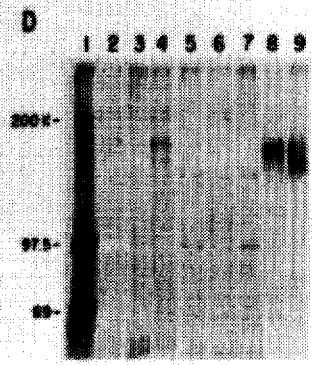

The following hybridoma cell lines were deposited with the American Type Culture Collection (ATCC), 12305 Parklawn Drive, Rockville, Md., 20852 under the Budapest Treaty and were accorded the following accession numbers:

Hybridoma cell line BD5-2d was accorded ATCC Accession number HB 9689 and deposited on Apr. 18, 1988.

Hybridoma cell line OD3 was accorded ATCC Accession number HB 10204 and deposited on Aug. 11, 1989.

Hybridoma cell line NB-3 was accorded ATCC Accession number HB 10205 and deposited on Aug. 11, 1989.

Hybridoma cell line TA-1 was accorded ATCC Accession number HB 10206 and deposited on Aug. 11, 1989.

DETAILED DESCRIPTION OF THE INVENTION

The terms human neu, c-erbB-2, HER-2/neu, and HER-2 are used interchangeably herein.

The term oncogene, as used herein, refers to a gene altered, in some fashion or by some mechanism, such that it contributes to converting a normal cell to a cancer cell. For example, the rat neu oncogene appears to contribute to malignancy in rats through a point mutation occurring in the transmembrane domain. On the other hand, the term human neu oncogene has been used to describe the human neu proto-oncogene which is believed to be altered in some way to contribute to malignancy in humans through over-expression of the human neu gene product. It has been shown that overexpression of the normal human c-erbB-2 protein leads to transformation of NIH/3T3 cells. (Di Fiore et al., Science, 237:178–182 (1987)).

The term "human neu gene product" refers to a growth factor receptor-like glycoprotein having an intracellular tyrosine kinase domain, a transmembrane domain and an extracellular domain which is produced by the human neu gene. This protein has been reported to have a molecular weight of about 185 or 190 kilodaltons. The abbreviation "p185" will be used interchangeably herein with the term human neu gene product.

The term "substantially purified" means synthesized or, if naturally occurring, isolated free of other cellular components with which it is normally associated.

While the function of human c-erbB-2 protein in normal growth and differentiation of cells remains unknown, it appears that the increased expression of a growth factor-receptor like protein encoded by the human c-erbB-2 gene might play an important role in the initiation or progression of neoplasia.

One of the important aspects of this invention concerns a human neu related protein which is detectable in a human biological fluid such as blood, serum, plasma, urine, cerebrospinal fluid, supernatant from normal cell lysate, supernatant from preneoplastic cell lysate, supernatant from neoplastic cell lysate, supernatants from carcinoma cell lines maintained in tissue culture, and breast aspirates.

More specifically, this invention concerns a substantially purified p100 which is a human neu related protein having a molecular weight in the range from about 97,000 daltons to about 115,000 daltons which corresponds substantially to the extracellular domain of the human neu gene product, the protein being detectable in a biological fluid such as those described above. The term "corresponds substantially" provides for conservative additions, deletions and/or substitutions.

It is believed that p100 is a cleavage/degradation product of p185. However, it is also possible that p100 may be independently synthesized. It is also possible that p100 may be further modified and/or cleaved.

The molecular weight range of p100 was determined using an immunoblot format or immunoprecipitation format as described below.

This invention also concerns a method of detecting preneoplastic or neoplastic cells in a human which comprises testing a biological fluid from a human for the presence of a p100 by:

(a) contacting the fluid with at least one monoclonal antibody which is capable of binding the protein, and (b) determining whether antibody binding has occurred.

In another embodiment this invention concerns an immunoassay for detecting or quantifying the presence of p100 which comprises (a) reacting the fluid with at least one first monoclonal antibody which is capable of binding to p100;

(b) reacting the product of step (a) with at least one detectably-labeled second monoclonal antibody which is capable of binding to p100 at an epitope different from the epitope bound by the first antibody; and (c) detecting or quantifying the product of step (b).

The monoclonal antibodies which can be used to detect p100 constitute another aspect of this invention.

Immunoreactive fragments of these antibodies can also be used to practice the invention.

These monoclonal antibodies or immunoreactive fragments thereof are specific for the extracellular domain of p185 as is shown below. Briefly, these antibodies were generated by immunizing mice using a protocol consisting of administering an NIH 3T3 cell line, cyclophosphamide, and a transfected NIH 3T3 cell line which expressed the full length human neu gene product. This procedure is set forth in greater detail below.

In accordance with this invention, an antibody or cocktail of antibodies can be used for detection. These antibodies can be labeled directly with a reporter or indirectly with a member of a specific binding pair using conventional techniques.

Specific binding pairs can be of the immune or non-immune type. Immune specific binding pairs are exemplified by antigen-antibody systems of hapten/anti-hapten systems. There can be mentioned fluorescein/anti-fluorescein, dinitrophenyl/anti-dinitrophenyl, biotin/anti-biotin, peptide/anti-peptide and the like. The antibody member of the specific binding pair can be produced by customary methods familiar to those skilled in the art. Such methods involve immunizing an animal with the antigen member of the specific binding pair. If the antigen member of the specific binding pair is not immunogenic, e.g., a hapten, it can be covalently coupled to a carrier protein to render it immunogenic.

Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent 1-ethyl-3-(dimethyl-aminopropyl)-carbodiimide (EDAC).

Homobifunctional crosslinkers, including the bifunctional imidoesters and bifunctional N-hydroxysuccinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labeled antibody, detectably-labeled antibodies, or detectably-labeled member of the specific binding pair is coupled to a reporter which can be a radioactive isotope, enzyme, fluorogenic, chemiluminescent or electrochemical materials. Two commonly used radioactive isotopes are $^{125}I$ and $^{3}H$. Standard radioactive isotopic labeling procedures include the chloramine T, lactoperoxidase and Bolton-Hunter methods for $^{125}I$ and reduction methylation for $^{3}H$.

Enzymes suitable for use in this invention include, but are not limited to, horseradish peroxidase, alkaline phosphatase, β-galactosidase, glucose oxidase, luciferase, β-lactamase, urease and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, Immunochemistry 8, 871 (1971), Avrameas and Ternynck, Immunochemistry 8, 1175 (1975), Ishikawa et al., J. Immunoassay 4(3):209–327 (1983) and Jablonski, Anal. Biochem. 148:199 (1985).

Labeling can be accomplished by indirect methods such as using spacers or other members of specific binding pairs. An example of this is the detection of a biotinylated antibody with unlabeled streptavidin and biotinylated enzyme, with streptavidin and biotinylated enzyme being added either sequentially or simultaneously. Thus, according to the present invention, the antibody used to detect can be detectably-labeled directly with a reporter or indirectly with a first member of a specific binding pair. When the antibody is coupled to a first member of a specific binding pair, then detection is effected by reacting the antibody-first member of a specific binding complex with the second member of the binding pair which is labeled or unlabeled as mentioned above.

Moreover, the unlabeled detector antibody can be detected by reacting the unlabeled antibody with a labeled antibody specific for the unlabeled antibody. Such an anti-antibody can be labeled directly or indirectly using any of the approaches discussed above. For example, the anti-antibody can be coupled to biotin which is detected by reacting with the streptavidin-horseradish peroxidase system discussed above.

One of the preferred embodiments of this invention utilizes biotin. The biotinylated antibody is in turn reacted with streptavidin-horseradish peroxidase complex. Ortho-phenylenediamine, 4-chloro-naphthol, or tetramethylbenzidine (TMB) can be used to effect chromogenic detection.

The preferred immunoassay format for practicing this invention is a forward sandwich assay in which the capture reagent has been immobilized, using conventional techniques, on the surface of the support.

Suitable supports used in assays include synthetic polymer supports, such as polypropylene, polystyrene, substituted polystyrene, e.g., aminated or carboxylated polystyrene; polyacrylamides; polyamides; polyvinylchloride, etc.; glass beads; agarose; nitrocellulose, etc.

The examples discussed below are intended to illustrate the invention and should not be construed as limitations.

EXAMPLE 1

Production of neu-Specific Monoclonal Antibodies

A. Production of Hybridomas

The hybridomas described below were generated by immunization of mice with viable cells (the 18-3-7 cell line described below) which express the full length protein encoded by the human neu gene, i.e., p185. Using the full length protein presented by viable cells as the immunogen, it is possible to generate a collection of monoclonal antibodies with specificities that span the entire length of the extracellular domain of the protein. This is as opposed to the use of peptide immunogens, or short polypeptides generated by prokaryotic systems, which present only a limited number of epitopes from the original protein, and hence raise an immune response of limited specificities. Furthermore, by presenting the protein antigen in what is believed to be its native state, the immune system will be responding to an antigen which most closely resembles that which will be seen when the antibodies are later used for diagnostic or therapeutic applications.

B. Generation of 18-3-7 Cells 18-3-7 cells are a transfected NIH 3T3 cell line that express full length normal human neu protein. The human neu gene is expressed by a Murine leukemia virus LTR (promoter and enhancer). This cell line exhibits all the characteristics of transformed NIH 3T3 cells. They grow in soft agar, form tumors in nude mice, and display altered morphological characteristics. This cell line was used as the immunogen for the isolation of anti-human neu specific monoclonal antibodies.

The pLJ retroviral vector was modified to remove the polyoma early region, thereby eliminating the endogenous transforming activity of the pLJ vector. Construction of the modified vector is shown in FIG. 1. The modification was accomplished by restricting pLJ with Apa I and isolating the 6300 base pair fragment, and recircularizing it with $T_4$ ligase. The resulting plasmid (pdelta LJ or AbT 5009, shown in FIG. 1) was digested at the unique Bam HI site, filled with Klenow, and ligated to a Klenow treated NcoI-HindIII fragment containing the entire human neu protein coding region. The resulting plasmid (pdelta LJ neu or pAbT 577, shown in FIG. 1) was transfected into NIH 3T3 cells by the calcium phosphate precipitation procedure. Transfected cells were selected in G418 (pdelta LJ has a SV40 promoted neo® gene). The colonies were screened for neu expression by RNA dot blots. 18-) 3-7 was one of the highest expressors out of approximately 50 screened.

C. Immunization of Mice

Two adult female Balb/c mice were immunized intraperitoneally (I.P.) with $1.4 \times 10^6$ viable NIH 3T3 cells per animal. This was followed immediately by an I.P. injection of cyclophosphamide in $H_2O$, 30 mg/kg. The cyclophosphamide treatment was repeated 24 and 48 hours after the primary injection. On day 14 following immunization, the mice were injected I.P. with $1.5 \times 10^6$ viable 18-3-7 cells. The animals were allowed to rest for another 14 days, at which time the entire sequence of injecting NIH 3T3 cells, cyclophosphamide, and 18-3-7 cells was repeated. Four days following the second injection of 18-3-7 cells, the animals were sacrificed and their spleens obtained for the first fusion A second, identical experiment was performed, in four female Balb/c mice and four female CB6 (Balb/cxC57BL/6) mice, using $1.8 \times 10^6$ NIH 3T3 cells, and $4.8 \times 10^6$ 18-3-7 cells per mouse in first round, and $8.5 \times 10^6$ NIH 3T3 cells and $2.7 \times 10^6$ 18-3-7 cells in the second round of immunizations.

D. Hybridoma Methodology

Hybridomas were produced by fusing cells from immunized mice with SP2/O myeloma cells (ATCC CRL 1518) by a polyethylene glycol (PEG) method. Spleens were removed asceptically from immunized mice, and a single cell suspension of the spleen cells was obtained by perfusing the spleen with serum-free media (DME). Spleen cells and SP2/O cells (harvested from a log phase growth culture) were mixed together at a ratio of 5:1, C spleen cell:myeloma cell. The cells were centrifuged at 200×g for 10 minutes at 4° C., and the supernatant removed by aspiration. After loosening the cell pellet by gently tapping the bottom of the tube, 1 ml of sterile, 37° C., 10% PEG in DME was added dropwise. The tube was gently swirled while adding the PEG over a 1.5 minute period. An additional 10 ml of 37° C. serum-free DME was then added dropwise, followed by another 20 ml of media. The suspension was then centrifuged at 200×g for 10 minutes at room temperature. Media was aspirated from the cell pellet, and media containing peritoneal macrophages ($2 \times 10^4$ cells per ml) in the presence of 20% fetal calf serum, 0.2 mM hypoxanthine, 0.4 μM aminopterin, and 0.032 mM thymidine (HAT media) was used to resuspend the cell pellet. (Peritoneal macrophages were obtained from unimmunized mice, either Balb/c or CB6, depending on which spleen cells were used for fusion. These cells were obtained by injecting and immediately removing serum-free media into the peritoneum of euthanized animals.) The post-fusion cells were resuspended in a final cell concentration (not including the peritoneal macrophages) of $5 \times 10^5$ cells/ml. One milliliter of this cell mixture was distributed to each well of 24 well plates.

E. ELISA Procedure and Preliminary Screening

Hybridomas which grew after the fusion procedure were initially screened for the secretion of anti-human neu antibodies by an ELISA assay on a cell lysate of 18-3-7 cells. Lysates were prepared by incubating freshly harvested 18-3-7 cells in the presence of a hypotonic lysis buffer (10 mM Tris, 10 mM KCl, 5 mM EDTA, pH 8.0) followed by the addition of Tritonx100 to a final concentration of one percent. A lysate of NIH 3T3 cells was prepared similarly for use as a negative control. Microtiter plates (Nunc, Immunoplate II) were coated overnight at room temperature with 50 μl of lysate, at a total protein concentration of 500 μg/ml. After aspirating to remove unbound antigen, ELISAs were performed by first incubating 50 μl of culture supernatant obtained from the viable hybridoma colonies in the antigen-coated microtiter wells. A 3 hour incubation at 37° C. was followed by 3 washes with a washing buffer (0.05% Tween 20, 20 mM Tris, pH 7.6) and then a one hour incubation at 37° C. with 50 μl horseradish peroxidase labeled goat anti-mouse IgG+gA+IgM (HRP-GAM-GAM). The wells were again washed three times with washing buffer, and the assay was developed by the addition of 50 μl of a tetramethylbenzidine (TMB) solution. This solution was prepared by dissolving 10 mg of TMB in 1 ml of dimethylsulfoxide (DMSO), and adding 100 μl of this solution to 5 ml of TMB buffer (0.1M sodium acetate, to pH 6.0 with 0.1M citric acid) along with the addition of 10 μl of 3% hydrogen peroxide. Color was allowed to develop for 5 minutes, at which time the enzymatic reaction. was stopped by adding 50 μl of 2N $H_2SO_4$. The optical density (OD) of the resulting yellow color was read at 450 nm on a microtfter plate reader. A positive reaction, as indicated by a greater yellow color developed on 18-3-7 cell-coated wells than on NIH 3T3 cell-coated wells, signaled that there was antibody present in the culture supernatant which recognized the human neu gene product.

F. Subcloing Hybridomas

Hybridomas which yielded positive results upon initial screening were expanded and cloned by limiting dilution to assure that the cells and resulting antibodies were indeed monoclonal. A feeder cell population was first prepared by obtaining thymocytes from 6 week old unimmunized mice, and making a single cell suspension at a concentration of $2 \times 10^4$ cells/ml in HAT media. Hybridoma colonies which tested positive for the presence of antibody to the human neu gene product were diluted in the media containing thymocytes to a concentration of 5 hybridoma cells/mi. Two hundred microliters of this solution was then delivered to each well of 96 well microtiter plates. Once colonies had grown, the supernatants were again tested for the presence of antibody to the human neu gene product. If the results were positive when tested by the ELISA assay as described above, the colonies were cloned by limiting dilution a second time.

Hybridomas which were obtained in the manner described above following the first fusion secrete monoclonal antibodies which have been designated BD5-2d, TA-1-1c, RC1-4c, NA3-6a, and OD3-10j. Following the second fusion, hybridomas were obtained which secrete antibodies named PB3, RC6-2, NB-3, ID5, and IB3-4.

G. Antibody Isotype and Subclass Determination

ELISA assays were performed to determine the isotype and light chain class of the antibody produced by the hybridomas, and to determine the IgG subclass. For this purpose, a kit was purchased from Boehringer Mannheim (Indianapolis, Ind.) which contained all of the necessary immunoreagents. Tissue culture supernatants obtained from the cloned hybridoma colonies were incubated on lysates of 18-3-7 cells as described above. This was followed by an incubation with goat antisera specific for mouse immunoglobulin isotypes, light chain classes, and IgG subclasses, and then with horseradish peroxidase labeled with swine anti-goat IgG as the second antibody. The assay was developed using ABTS (2,2'-azino-bis-[3-ethylbenzthiazoline-6-sulfonic acid]) as per the manufacturer's instructions, and the OD of the resulting green color was read at 405 nm.

Using this method, it was determined that 3 of the monoclonal antibodies from the first fusion, BD5-2d, RC1-4c, and TA-1-1c, are $IgG_1$/kappa antibodies, and NA3-6a, and OD3-10j are IgM/kappa antibodies. The monoclonal antibodies RC6-2, NB-3, ID5, and IB3-4 obtained from the second fusion are $IgG_1$/kappa and the antibody PB3 is $IgG_{2a}$/lambda.

H. Radioimmunoprecipitation

Immunoprecipitation of radioactively labeled 18-3-7 cells was done using each of the monoclonal antibodies to determine whether the antibodies recognized a protein of 185 kd molecular weight, the expected molecular weight of the human neu gene product. A near confluent monolayer of 18-3-7 cells (or NIH 3T3) cells in a 10 cm petri dish was incubated overnight in media containing 500 µCi of $^{35}$S-labeled cysteine. The cells were harvested the following morning, and were lysed in a detergent buffer (IP buffer: 1% Triton X-100, 1% sodium deoxycholate, 0.1% SDS, 10 mM Tris, 0.65M NaCl, pH 7.2) containing the protease inhibitors PMSF and soybean trypson inhibitor. Approximately 1 µCi of the labeled cell preparation was then incubated overnight at 4° C. with 500 µl of culture supernatant from each of the hybridomas. During this incubation period, 50 µg of purified rabbit anti-mouse IgG (Kirkegaard & Perry Labs) was mixed with 50 µl of a 1:1 slurry of Protein A-Sepharose (Pharmacia) in IP buffer overnight at 4° C. The excess rabbit antibody was removed by washing the Protein A-Sepharose once with IP buffer, and the slurry was then added to the incubation mixture containing the labeled cells and the monoclonal antibody. This mixture was allowed to react overnight at 4° C. The Protein A-Sepharose was pelleted by centrifugation and was washed four times with IP buffer, followed by one wash with TBS (10 mM Tris, 150 mM NaCl, pH 8.2), and the pellet was allowed to dry. Each pellet was resuspended in 50 µl of sample buffer for SDS gels (10 mM Tris, 4% SDS, 20% glycerol, 10% 2-mercaptoethanol, 0.04% bromphenol blue). One-half of each of the samples was run on SDS polyacrylamide gels, using a 4.5% acrylamide stacking gel, and a 7% separating gel. The gels were dried and then autoradiog rapbed.

Results of the immunoprecipitations indicated that all of the monoclonal antibodies recognized a protein of approximately 185 kd molecular weight (p185) in the 18-3-7 cells which was not present in the NIH 3T3 cells. This was determined by the presence of a dark band on the autoradiograph which corresponded to the distance travelled in the gel by a 185 kd molecular weight protein as indicated by standard protein markers. A similar experiment was done using SKBR-3 cells (a human breast carcinoma) and A431 cells (a human epidermoid carcinoma). The SKBR-3 cells have been shown by other investigators to express high levels of the human neu gene product, and immunoprecipitations with the monoclonal antibodies described above yielded confirming results. The band observed migrated the same distance as the band which was precipitated from the labeled 18-3-7 cells. Based upon these experiments and the immunoblot analysis described below it was concluded that the monoclonal antibodies raised to the 18-3-7 cells were specific for the human neu gene product, and did not cross react with human EGFR.

FIG. 2 presents immunoprecipitation results.

Panel A: Immunoprecipitation of 18-3-7 and NIH/3T3 cell lysates with the IgG monoclonal antibodies. Lane 1 contains molecular weight standards. Lanes 2, 4, 6, 8 and 10 contain 18-3-7 lysates, and Lanes 3, 5, 7, 9 and 11 contain NIH/3T3 lysates. Lanes 2 and 3: precipitation with TA1. Lanes 4 and 5: precipitation with BD5. Lanes 6 and 7: precipitation with NB3. Lanes 8 and 9: precipitation with PB3. Lanes 10 and 11: precipitation with MOPC-21.

Panel B: Immunoprecipitation of 18-3-7 and NIH/3T3 cell lysates with the IgM monoclonals. Lane 1 contains molecular weight standards. Lanes 2, 4 and 6 contain 18-3-7 lysates; Lanes 3, 5 and 7 contain NIH/3T3 lysates. Lanes 2 and 3: precipitation with OD3. Lanes 4 and 5: precipitation with NA3. Lanes 6 and 7: precipitation with TEPC 183.

Panel C: Immunoprecipitation of SKBR-3 and A-431 cell lysates with IgG monoclonals. Lane 1 contains molecular weight standards. Lanes 2, 4, 6, 8, 10 and 12 contain SKBR-3 lysates. Lanes 3, 5, 7, 9, 11 and 13 contain A-431 lysates. Lanes 2 and 3: precipitation with TA1. Lanes 4 and 5: precipitation with BD5. Lanes 6 and 7: precipitation with PB3. Lanes 8 and 9: precipitation with NB3. Lanes 10 and 11: precipitation with MOPC 21. Lanes 12 and 13: precipitation with rabbit anti-EGFR.

Panel D: Immunoprecipitation of SKBR-3 and A-431 cell lysates with IgM monoclonals. Lane 1 contains molecular weight standards. Lanes 2, 4, 6 and 8 contain SKBR-3 lysates. Lanes 3, 5, 7 and 9 contain A-431 lysates. Lanes 2 and 3: precipitation with OD3. Lanes 4 and 5: precipitation with NA3. Lanes 6 and 7: precipitation with TEPC 183. Lanes 8 and 9: precipitation with rabbit anti-EGFR.

I. Immunoblot

Lysates of SKBR-3 cells (ATCC HTB 30) and A-431 cells (ATCC CRL 1555) were electrophoresed on 1.5 mm thick 7% SDS-polyacrylamide gels, using a 4.5% stacking gel. The separated proteins were transferred onto nitrocellulose (Schleicher & Schuell) using the BioRad Transblot apparatus. The nitrocellulose filter was then blocked for 1 hour in Blotto (3% dry milk, 2% normal goat serum, 0.1% Tween-20 in PBS) and incubated for 3 hours at room temperature with either 0.5 µg/ml OD3, or 2 µg/ml PB3 (both diluted with Blotto), or with 20 µg/ml 291-3A (in culture supernatant). 291-3A is an anti-EGFR monoclonal antibody generated using a peptide derived from the tyrosine kinase domain of EGFR. (291-3A was a gift from Randall Schatzmann, Syntex Research, Palo Alto, Calif.) Filters were rinsed 3 times in a High Salt wash buffer (20 mM Tris-HCl, 1M NaCl, 0.05% Tween-20, pH 7.6) and were then incubated with alkaline phosphatase labeled goat anti-mouse IgG+IgA+IgM (Kirkegaard & Perry Labs) for 1 hour at room temperature. They were washed again three times with the high salt wash buffer, and the bands were visualized using a BCIP NBT substrate kit (Kirkegaard & Perry Labs).

Figures 3A, 3B, 3C:
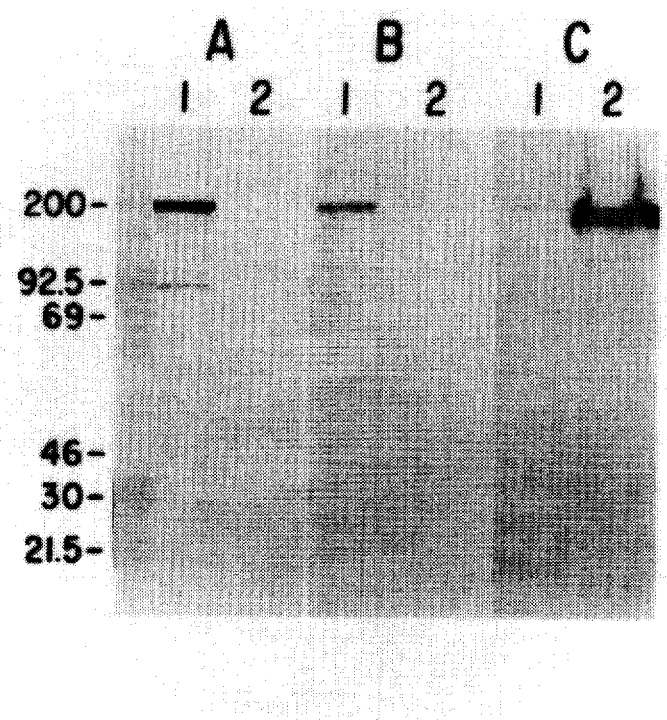
FIGS. 3A, 3B, and 3C presents immunoblot results for monoclehal antibodies OD3 and PB3.

In all cases, Lane 1 contains 80 µg of SKBR-3 cell lysate and Lane 2 contains 80 µg of A-431 lysate, separated by SDS-PAGE on a 7.5% SDS-polyacrylamide gel, and electrophoretically transferred to nitrocellulose. Immunoblot results are presented in FIGS. 3A, 3B, and 3C. FIG. 3A detection with 0.5 µg/ml purified OD3FIG. 3B detection with 2 µg/ml purified PB3; and FIG. 3C detection with 20 µg/ml purified 291-3A.

J. Immunofluorescence

Cell lines were grown to confluence on 8-chambered LabTek tissue culture slides (Miles Scientific) overnight. They were briefly washed in Dulbecco's PBS (containing $Ca^{++}$ and $Mg^{++}$) and were fixed with 3% formalin for 30 minutes at room temperature. A 1:50 dilution of TA-1 ascites fluid (diluted in 50% normal goat serum) was incubated with the cells for 1 hour at room temperature. The slides were washed again with PBS, and were then incubated for 1 hour at room temperature with fluorescein labeled goat anti-mouse IgG (Cappel).

Immunofluorescent results are presented in FIG. 4: panel (a) 18-3-7 cells; panel (b) NIH3T3 cells; panel (c) SKBR-3 cells and panel (d) A-431 cells. Positive fluorescent staining was observed on 18-3-7 and SKBR-3 cells. No staining was observed on NIH3T3 and A-431 cells.

K. Flow Cytometry

Cells were harvested from culture, washed once, and resuspended to a concentration of $2 \times 10^6$ viable cells per sample in Leibovitz L-15. They were then incubated with 1 µg of purified TA-1 or with the isotype-matched control MOPC-21 for 1 hour at 4° C. The cells were washed three times with PBS and incubated with 1 µg of goat anti-mouse Ig-FITC for 1 hour at 4° C. This incubation was followed by three additional washes in PBS. The cells were analyzed using an EPICS V flow cytometer with an argon laser tuned to 488 nm. Discriminators were set such that <5% of the cells were positive with the isotype-matched control antibody. The percentage of cells positive and the mean fluorescence intensity for each histogram was determined using the Easy 88 software (Coulter). In all panels: MOPC21 (M21) is represented by . . . and TA1 is represented by __.

Figure 5A:
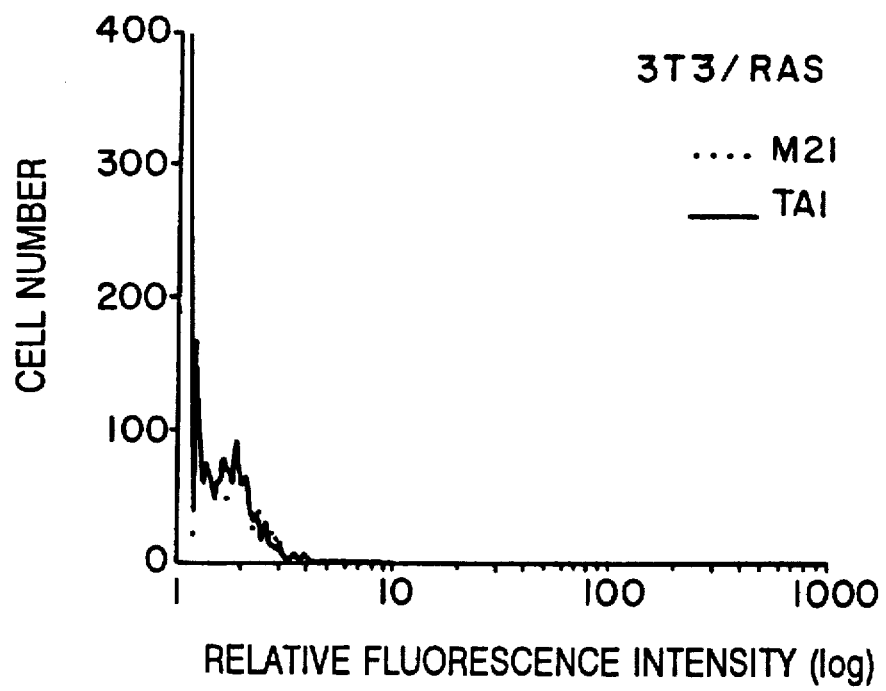
FIGS. 5A, 5B, 5C, and 5D presents flow cytometric results.
Figure 5B:
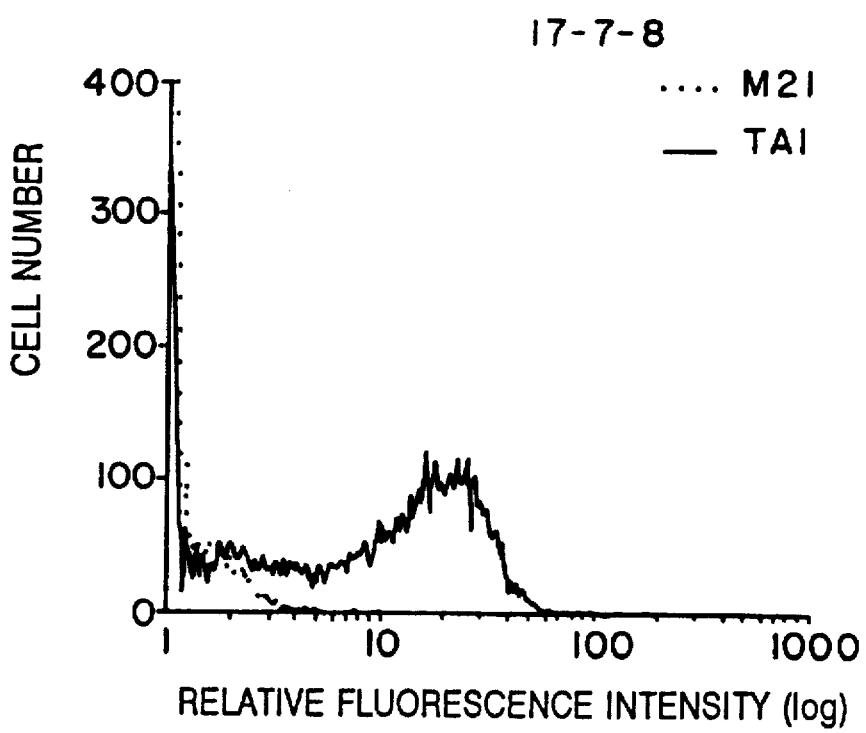
Figure 5C:
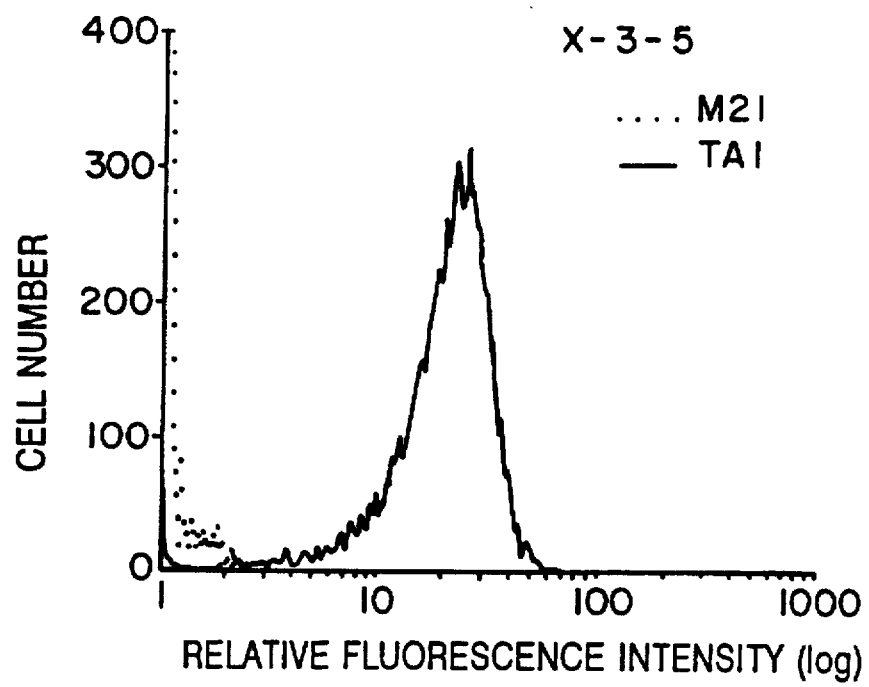
Figure 5D:
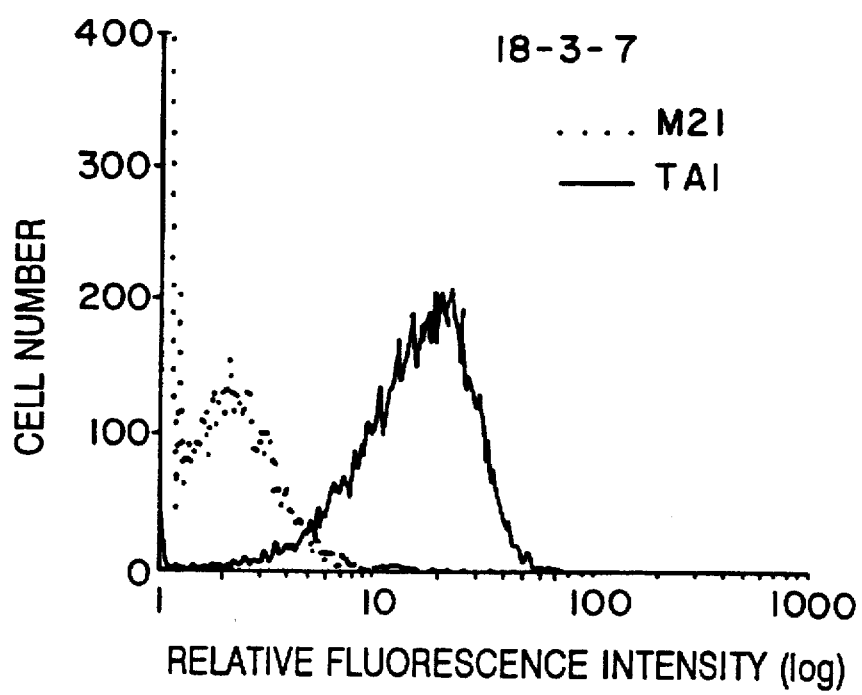

Flow cytometric results are presented in FIGS. 5A–5D: FIG. 5A NIH/3T3/ras, an NIH/3T3 cell line transfected with the ras oncogene. FIG. 5B: 17-7-8, an NIH/3T3 cell line Co-transfected with the ras and human neu oncogenes. FIG. 5C: X-3-5, an NIH/3T3 cell line co-transfected with the ras and human neu oncogenes. FIG. 5D: 18-3-7, an NIH/3T3 cell line transfected only with the human neu oncogene. The p185-positive cell lines demonstrated a mean-fluorescence intensity which was approximately 10-fold greater than background.

Table 1 summarizes the results obtained from the above-described evaluations.

TABLE 1

| | | Characteristics of Mabs | | | |
|---|---|---|---|---|---|
| | Isotype | | Reactivity* | | |
| Mab | and Subclass | Western Blot | IP** | Fluorescence+ | Flow Cytometry |
| BD5 | IgG$_1$/κ | − | + | + | + |
| RC1 | IgG$_1$/κ | − | + | + | + |
| TA-1 | IgG$_1$/κ | − | + | + | + |
| NA3 | IgM/κ | − | + | ND*** | ND |
| OD3 | IgM/κ | + | + | ND | + |
| PB3 | IgG$_{2a}$/λ | + | + | ND | + |
| RC6 | IgG$_1$/κ | − | + | ND | ND |
| NB-3 | IgG$_1$/κ | − | + | ND | + |
| ID5 | IgG$_1$/κ | − | + | ND | + |
| IB3 | IgG$_1$/κ | − | + | ND | ND |

*All assays were performed as described.
**IP-immunoprecipitation
+ Fluorescence-immunofluorescence
***ND-not done

EXAMPLE 2

Demonstration that monoclonal antibodies TA-1 and NB-3 recognize distinct epitopes on the p185 molecule Competitive enzyme immunoassays were performed to demonstrate that anti-human neu monoclonal antibodies TA-1 and NB-3 bind to different epitopes on the extracellular domain of p185. This was shown by co-incubating the two antibodies with p185 and demonstrating that neither can inhibit the specific binding of the other.

Methods

Microtiter plates were coated with 50 µl of a cell lysate of 17-3-1-3 cells which were used as a source of p185, at a total protein concentration of 10 µg/ml. (McKenzie et al., 1989 Oncogene 4:543–548). The 17-3-1-3 cell line is an NIH 3T3 cell line stably transfected with the full length human neu gene. The plates were coated overnight at room temperature, and then washed three times with ELISA wash (0.05% Tween 20 in phosphate buffered saline, pH 7.4). Serial two-fold dilutions of the competing antibody, from 4 µg/ml to 0.03 µg/ml, was then added to the wells and incubated for 1 hour at 37° C. The plate was washed three times and the biotinylated test antibody was added to each well. Either a 1:800 dilution of 1 mg/ml biotinylated-TA-1, or a 1:500 dilution of 1 mg/ml biotinylated-NB-3, was used. Following a 3 hour incubation at 37° C., the plate was washed again three times with ELISA wash, and a 1:4000 dilution of avidin-labeled horseradish peroxidase (avidin-HRP; Sigma) was then added and incubated for 1 hour at 37° C. The plate was washed a final three times, was developed using tetramethylbenzidine (TMB; Sigma; 10 mg TMB in 1 ml dimethylsulfoxide, added to 50 ml of a 0.1M acetate buffer, pH 6.0, plus 100 µl of 3% $H_2O_2$), and the reaction stopped after 5 minutes using 2.5N $H_2SO_4$. The resulting yellow color was read on an ELISA plate reader at 450 nm.

Results

Figure 6:
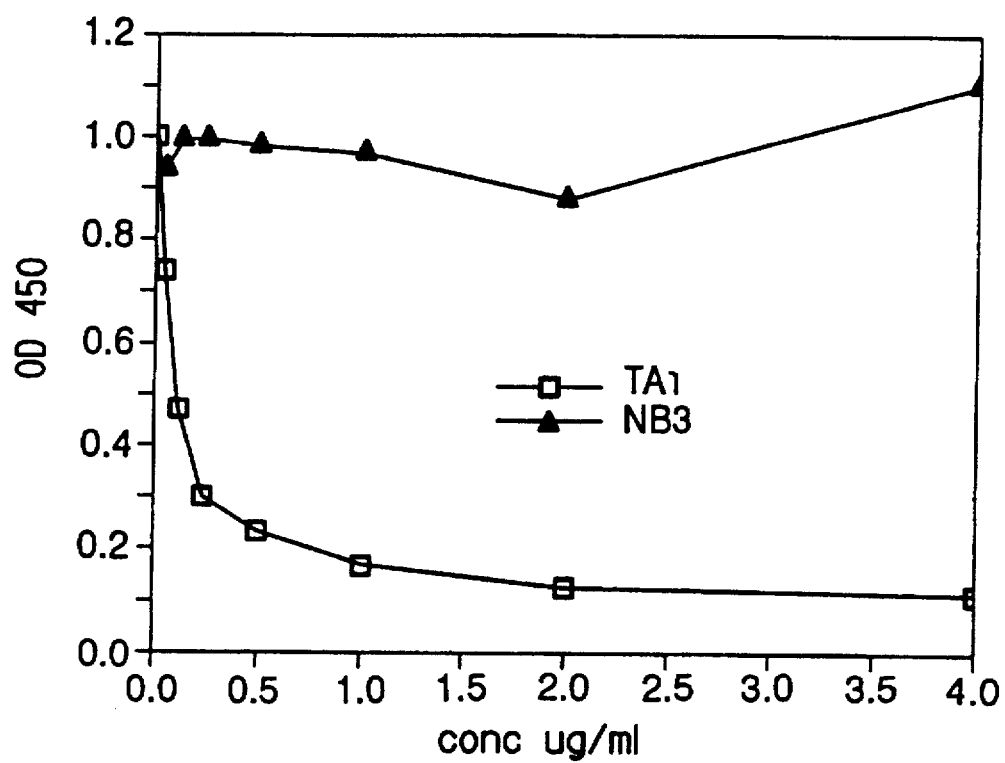
FIG. 6 shows the binding curves when TA-1 and NB-3 were used to compete with the binding of biotinylated TA-1.
Figure 7:
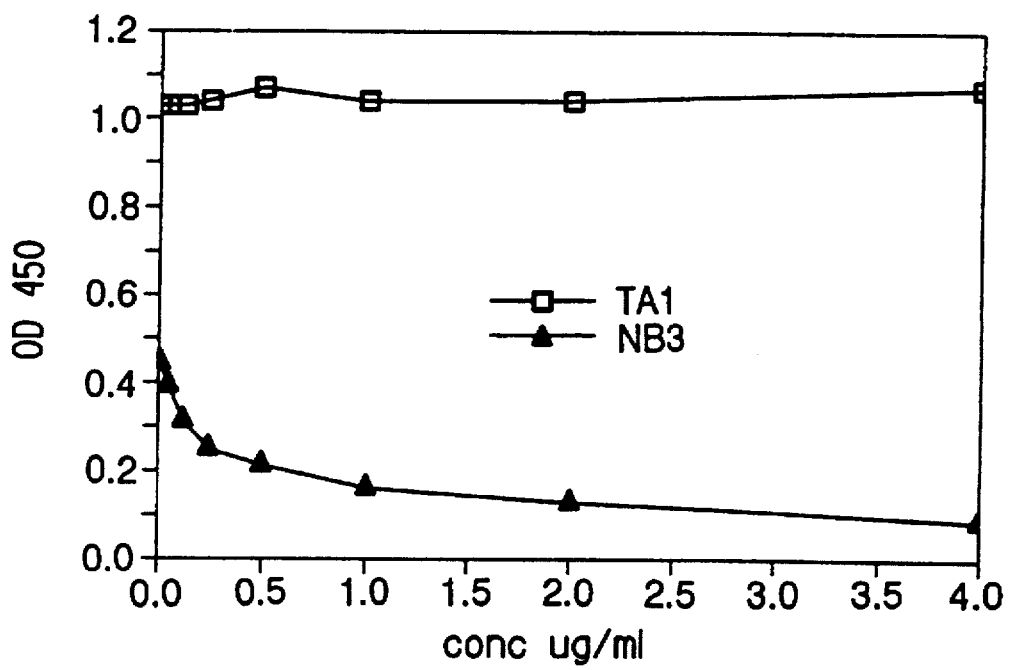
FIG. 7 shows the binding curves when TA-1 and NB-3 were used to compete with the binding of biotinylated NB-3.

FIG. 6 shows the binding curves with TA-1 and NB-3 were used to compete with the binding of biotinylated-TA-1. It can be seen that increasing amounts of unlabeled TA-1 completely inhibits the binding of biotinylated-TA-1 (open squares), as indicated by the reduction of the OD 450 signal. Increasing amounts of NB-3 (closed triangles) had no effect. FIG. 7 shows the curves when TA-1 and NB-3 were used to compete with biotinylated-NB-3. In this case, increasing amounts of NB-3 (closed triangles) completely inhibited the binding of the biotinylated-NB-3, whereas TA-1 (open squares) had no effect.

These results indicated that the antibodies recognized two distinct epitopes on the human neu gene product.

EXAMPLE 3

Demonstration that the substance detected in biological fluids is related to p185

The SKBR-3 cell line is a continuous cell line which originated from a human breast tumor, and is known to express high levels of the human neu gene product, p185 (Kraus, et al. (1987), Embo J. 6:605–610). Monoclonal antibodies specific for p185 as described above were shown to detect a protein of approximately 100,000 daltons in the culture media removed from these cells. A competitive binding assay was performed in order to confirm that p100 was related to the human neu gene product, p185.

The p185 present in lysates of cells transfected with the neu gene was used to compete for antibody binding with a radiolabeled p100 in the SKBR-3 supernatant. The amount of anti-neu antibody used in the competition assay was titrated in order to demonstrate two points:

1. the amount of antibody was a limiting reagent in the assay, such that the unlabeled p185 and the radiolabelled p100 would actually compete for binding; and 2. the amount of antibody used was sufficient to visualize the radiolabelled p100 band following autoradiography.

One 10 cm petri dish containing subconfluent (approximately $5 \times 10^6$) SKBR-3 cells (ATCC HTB 30) was incubated with 500 μCi of $^{35}$S-cysteine (Du Pont) in cysteine-free media overnight at 37° C., 5% $CO_2$. The culture supernatant was used as the source of radiolabelled p100.

An NIH 3T3 cell line stably transfected with the full length human neu gene, and designated 17-3-1-3, was used as a source of p185. Cell lysates were prepared by scraping cells from 10 (15 cm) petri dishes into 10 ml of phosphate buffered saline (PBS). The cells were pelleted by centrifugation at 200×g for 10 minutes, the pellet resuspended in 5 ml of hypotonic lysis buffer (10 mM Tris, 10 mM KCl, 5 mM EDTA, pH 8.0), and then homogenized with a Dounce homogenizer. The homogenate was centrifuged at 200×g for 10 minutes, and the resulting supernatant was sonicated for 15 seconds. All remaining cellular debris was then removed by centrifugation in a micro-centrifuge, and the final supernatant was used as the cell lysate. Similarly, a lysate of nontransfected NIH 3T3 cells was prepared. Total protein concentration of each lysate was determined using a kit based on the Bradford method (BioRad), using BSA as a standard. The concentration of the 17-3-1-3 lysate was determined to be 2.69 mg/ml total protein, and the NIH 3T3 lysate was 1.01 mg/ml. The 17-3-1-3 lysate was used at a 1:3 dilution for these assays.

The amount of human neu related protein present in the SKBR-3 supernatant and the 17-3-1-3 lysate was determined by ELISA. The monoclonal antibody TA-1 was used to coat the wells of Nunc Immunoplates. This was followed by incubation with either the supernatant or the lysate, and then by incubation with biotinylated PB3 antibody ($IgG_2\kappa$). The assay was developed by a final incubation with avidin-labeled horseradish peroxidase (HRP), and tetramethylbenzidine (TMB) as the colorimetric substrate for HRP. This capture ELISA detected 3.72 OD units/ml of neu related protein in the culture supernatant from the SKBR-3 cells, and 1295 OD units/ml in the 17-3-1-3 lysate. The activity in the NIH 3T3 cell lysate was zero.

Protein A-Sepharose (Pharmacia) was swollen and washed with immunoprecipitation buffer (IP buffer: 1% Triton X-100, 1% sodium deoxy-cholate, 0.1% sodium dodecylsulfate, 10 mM Tris, 650 mM NaCl, pH 7.2), and resuspended 1:1 (vol/vol) in IP buffer.

Samples were prepared by mixing 103 μl of 17-3-1-3 lysate (diluted 1:3; approximately 45 OD units of neu activity) with 1 μg, 0.3 μg, 0.01 μg, or 0.003 μg of purified PB3 antibody. These were incubated overnight at 4° C. with mixing. Control samples were prepared by incubating 277 μl of NIH 3T3 lysates with PB3 in the same fashion. Following the overnight incubation, 1.028 ml of radiolabeled SKBR-3 supernatant (approximately 4 OD units of neu, and 4 μCi of total labeled material) was added to each sample. All samples were then incubated again overnight at 4° C. with gentle mixing. Following this second incubation, 50 μl of the Protein-A Sepharose slurry was added to each sample, and each was incubated with mixing for 1 hour at 4° C. The Sepharose was pelleted by centrifugation for 1 minute in a micro-centrifuge, and was washed 4 times by resuspending the Sepharose in 1 ml of IP buffer, vortexing briefly, and centrifuging for 30 seconds in the micro-centrifuge. The samples were washed a final time in TBS (Tris buffered saline, pH 7.5). Samples were air dried, resuspended in 30 μl of SDS-PAGE sample buffer, and then incubated at 100μ C. for 5 minutes. The entire sample was loaded and run on a 7% SDS-polyacrylamide gel. After the gel was fixed, it was rinsed with En$^3$Hance (Du Pont), and dried. An autoradiograph was produced by exposing X-OMAT AR film (Kodak) to the dried gel in the presence of an intensifying screen at −70° C. for 6 days.

Figure 14:
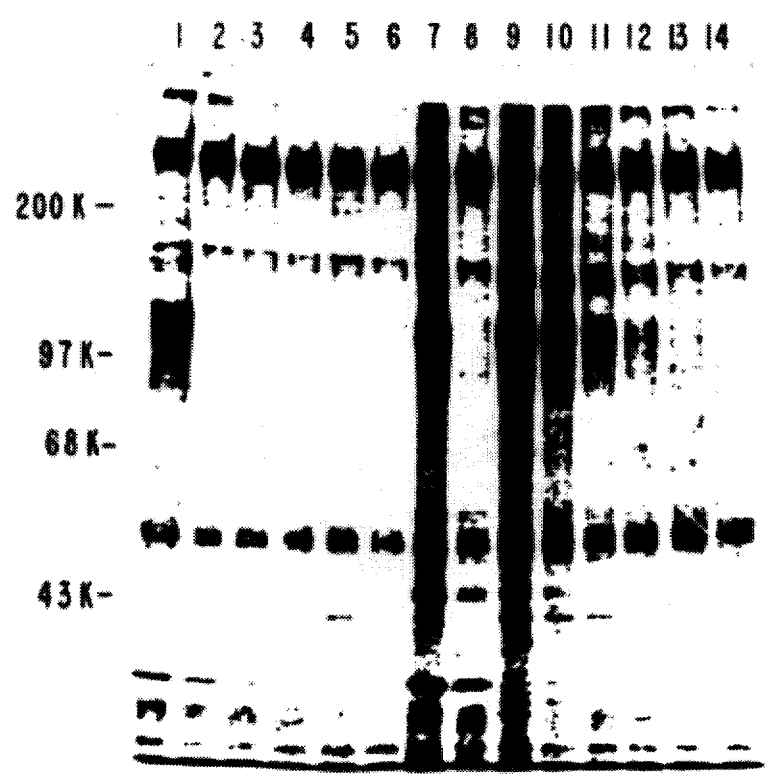
FIG. 14 presents immunoprecipitation results showing the relationship of p100 to p185.

Results are presented in FIG. 14.
Lane 1: 1 μg of PB3+17-3-1-3 lysate+SKBR-3 supernatant
Lane 2: 0.3 μg of PB3+17-3-1-3 lysate+SKBR-3 supernatant
Lane 3: 0.1 μg of PB3+17-3-1-3 lysate+SKBR-3 supernatant
Lane 4: 0.03 μg of PB3+17-3-1-3 lysate+SKBR-3 supernatant
Lane 5: 0.01 μg of PB3+17-3-1-3 lysate+SKBR-3 supernatant
Lane 6: 0.003 μg of PB3+17-3-1-3 lysate+SKBR-3 supernatant
Lane 7: 1 μg of PB3+SKBR-3 supernatant
Lane 8: 0.003 μg of PB3+SKBR-3 supernatant
Lane 9: 1 μg of PB3+NIH 3T3 lysate+SKBR-3 supernatant
Lane 10: 0.3 μg of PB3+NIH 3T3 lysate+SKBR-3 supernatant
Lane 11: 0.1 μg of PB3+NIH 3T3 lysate+SKBR-3 supernatant
Lane 12: 0.03 μg of PB3+NIH 3T3 lysate+SKBR-3 supernatant
Lane 13: 0.01μg of PB3+NIH 3T3 lysate+SKBR-3 supernatant
Lane 14: 0.003 μg of PB3+NIH 3T3 lysate+SKBR-3 supernatant The right half of the gel showed titration of the PB3 antibody in the presence of the NIH 3T3 lysate as the competitive agent. As there should be no competition between molecules present in the 3T3 lysate and the p100 protein, the disappearance of the band at 100,000 daltons as the antibody is titrated indicates that the antibody is becoming the limiting reagent.

The left side of the gel showed titration of the PB3 antibody in the presence of the 17-3-1-3 lysate. In all lanes, except the 1 μg PB3 sample, the p100 band was absent. This was particularly significant in the lanes which contained 0.3 μg and 0.1 μg of PB3, as there was still discernable band in the comparable samples when the NIH 3T3 lysate was used as the competitor. The presence of some p100 in the 1 μg PB3 sample indicated that the antibody was in such excess that it could bind the radiolabeled material as well as the unlabeled p185 which was added.

The disappearance of the p100 band when the 17-3-1-3 lysate was added indicated that the p100 molecule was indeed related to p185. The size correlated with the predicted molecular weight of the extracellular domain of the human neu gene product.

EXAMPLE 4

Detection of p100 in biological samples

These examples illustrate detection of the human neu related protein in cell lysates, tumor lysates, and in human blood plasma and sera.

A. Capture Immunoassay: General Protocol

Polystyrene plates (Nunc) were coated with either 20 microgram per milliliter (μg/ml) of an anti-neu monoclonal antibody (Mab), a combination of anti-neu Mabs, or a polyclonal antibody for the purpose of capturing human neu protein from various biological specimens. Mabs were diluted in 0.1M carbonate buffer (pH 9.6) and 100 microliters (μl) added to each well of the microtiter plate. The plates were then incubated overnight at 4° C.

After incubation, the coating material was decanted from the plates and 250 μl of blocking buffer (PBS with 2% bovine serum albumin (BSA), 10% Beta-lactose and 0.01% thimerosal) was added to each well. The blocking buffer was decanted and 250 μl of fresh blocking buffer added to each well in order to block sites on the microtiter wells not coated with the anti-human neu antibody. Plates were incubated for 2 hours at room temperature. The blocking buffer was decanted and plates blotted with paper towels. Plates were dried overnight in a hood at room temperature and then stored covered at 4° C. until use.

Specimens to be evaluated for the human neu protein consisted of lysates prepared from normal, preneoplastic or neoplastic cells or human body fluids such as serum, plasma or urine. The specimen was then added to the antibody coated wells in order to capture the human neu protein from the specimen. The plates were incubated overnight at room temperature. After incubation, the plates were washed six times with Du Pont Plate Wash Buffer (PBS, 0.05%, Tween 20) and a Dynatech Plate Washer in order to remove unbound biological specimen.

Another anti-human neu Mab coupled to biotin was added to each well and incubated for 30 minutes at room temperature. Plates were then washed six times with Du Pont Plate Wash Buffer. To detect the biotinylated anti-neu Mab, streptavidin-horseradish peroxidase was added at a 1:2500 dilution and allowed to incubate for 15 minutes at room temperature. Plates were then washed six times with Du Pont Plate Wash Buffer. To complete the reaction, the substrate orthophenylenediamine (OPD) was added for 1 hour at room temperature. The reaction was stopped with sulfuric acid and the optical density was determined using a Molecular Devices Plate Reader at a wavelength of 490 nm.

B. Detection of p185 from cell and tumor lysates using capture assays

Figure 8:
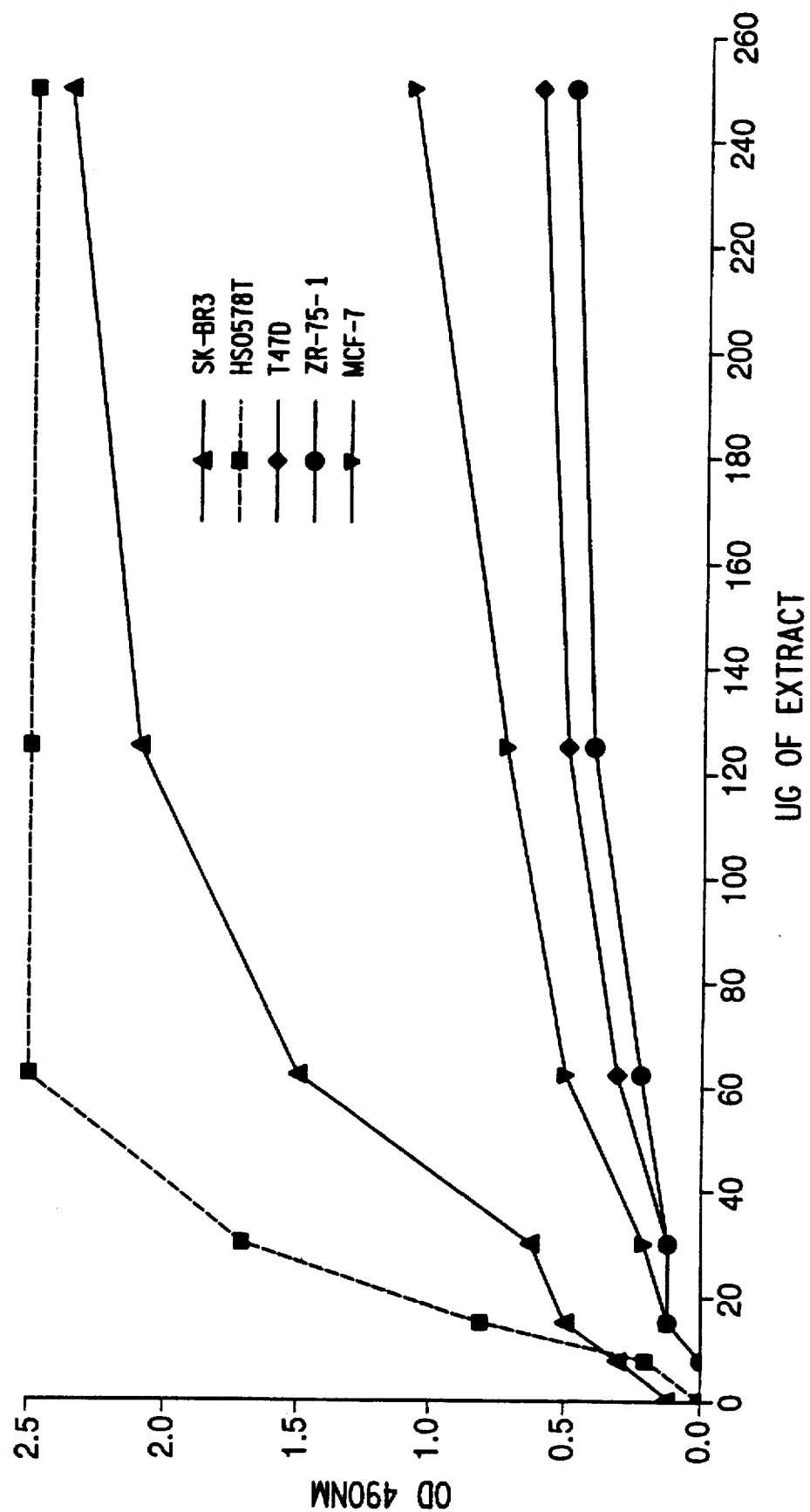
FIG. 8 shows results of a capture immunoassay in which lysates from a variety of human breast carcinoma cell lines were tested for the presence of the neu related protein using the capture ELISA system. An anti-human neu monoclonal antibody (TA-1) was used to capture neu related protein and anti-human neu monoclonal antibody, NA-3, was biotinylated and detected using streptavidin-horseradish peroxidase (SA-HRP).

Several capture immunoassays have been performed to determine usefulness of this assay on biological materials. FIG. 8 shows the results of a capture immunoassay in which the first antibody is TA-1 and the second antibody is biotinylated NA-3. Cell lysates were prepared from several human tumor cell lines. neu RNA levels have been published for several of these cell lines (SK-BR-3, ZR-75-1, MCF-7). The relative levels of human neu detected by this assay are in agreement with the published RNA data. The results of these assays and several others (not shown) using cell lines with known levels of human neu indicated this assay can be used to determine the relative level of human neu in cell lysates. Results also indicated that differences in expression of human neu related protein can be used to classify the carcinoma cell lines shown in FIG. 8.

Figure 9:
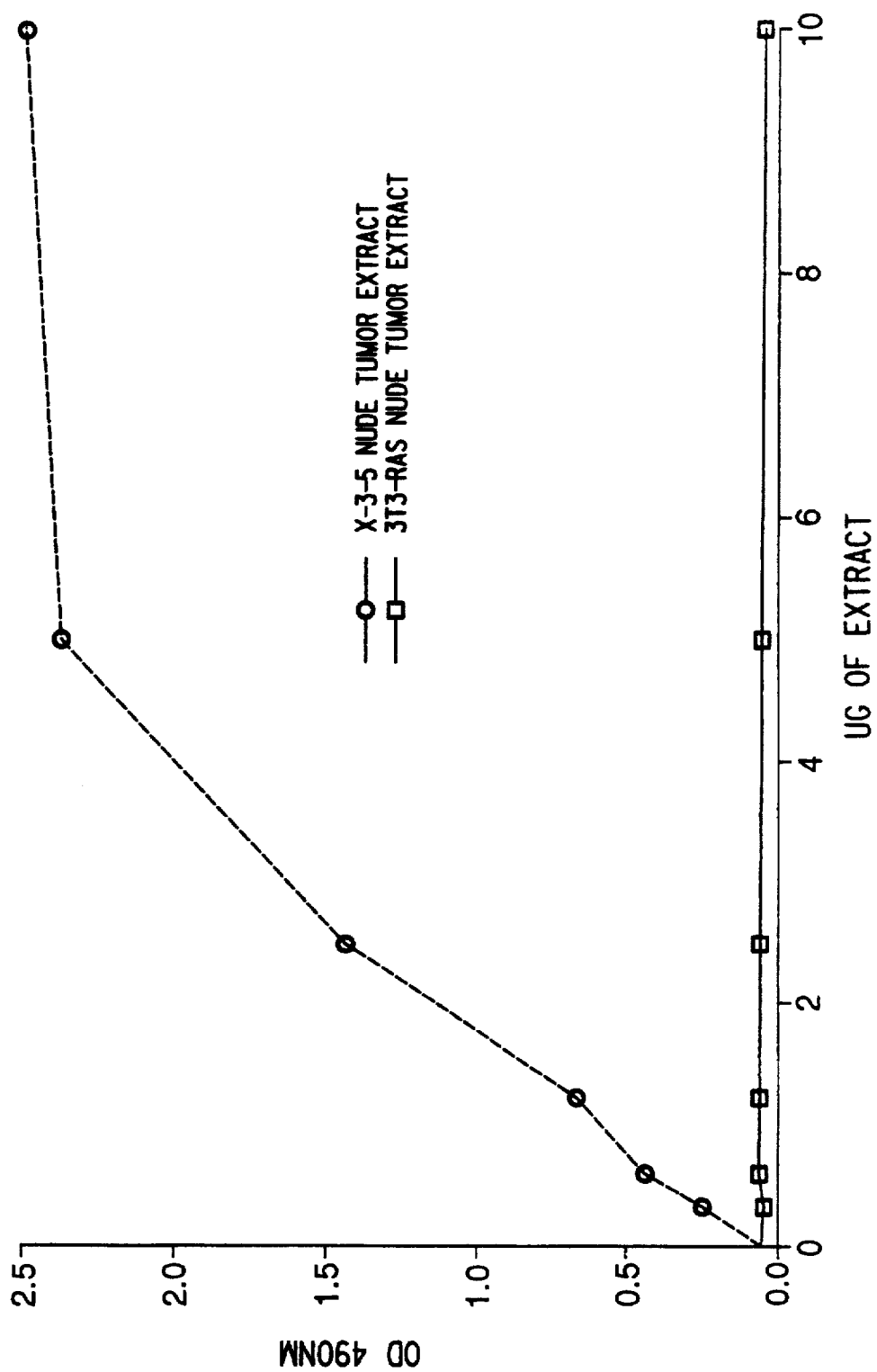
FIG. 9 shows results (microgram of tumor lysate vs. optical density) of a comparison between tumor lysate of a nude mouse tumor expressing neu (X-3-5) and tumor lysate of a neu negative tumor (3T3/ras). The assay was performed with an anti-human neu monoclonal antibody designated NB-3 as the capture reagent and the anti-human neu monoclonal antibody TA-1 was biotinylated and detected using SA-HRP.

In order to determine if this assay could detect human neu in tumor lysates, tumors that either expressed human neu (X-3-5) or did not express human neu (3T3 ras) were grown in nude mice. The two NIH 3T3 derived cell lines are isogenic except that X-3-5 expressed at the human neu gene. FIG. 9 shows the results of a capture immunoassay using NB-3 as the capture antibody and biotinylated TA-1 as the detector antibody. A human neu related gene product was detected in the lysate of the X-3-5 tumor but not in the lysate of the 3T3-ras tumor, indicating the assay can specifically detected human neu in tumor lysates.

Figure 10:
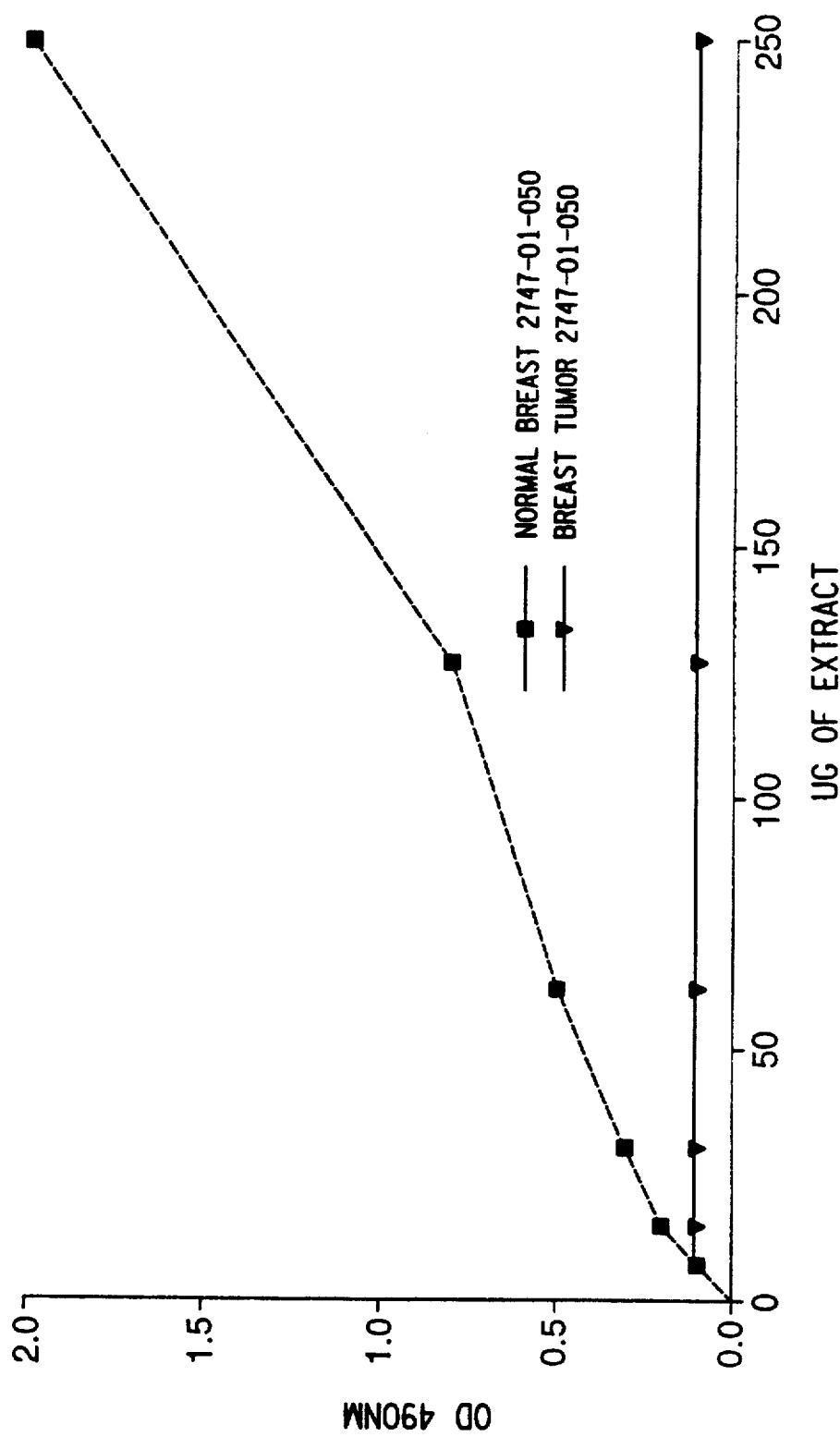
FIG. 10 shows the results of a capture immunoassay of cell lysates prepared from a normal piece of human breast tissue (2747-01-050) or a breast carcinoma (2747-01-050) and tested for the presence of neu related protein using the capture format. The assay was performed with an anti-human neu monoclonal antibody designated TA-1 as the capture reagent and the monoclonal antibody BD-5 was coupled to biotin and detected using SA-HRP.

Several investigators have shown that many human breast tumors express human neu at high levels. In order to determine if human neu can be detected in human breast tumors, two samples from the same individual were prepared. Lysates were prepared from a human breast tumor (2747-01-050) and from normal breast tissue (2747-01-050) from the same patient. In this assay TA-1 was used as the first antibody and biotinylated BD-5 was used as the detector antibody. FIG. 10 shows that human neu can be detected in the tumor.

These assays showed that the neu capture immunoassay specifically detected a human neu related gene product from either cell or tumor lysates. The data also indicated the assay can determine relative levels of neu between samples.

Lysates of human breast tumor and normal breast tissue (2747-01-050) from the same patient were evaluated by immunoblot. The immunoblot results showed that the neu related protein detected from the breast carcinoma lysate was p185.

C. Detection of P100 in blood plasma and sera

These examples illustrate detection of human neu in sera and plasma from mice and humans bearing neoplastic tumors.

In order to determine if human neu can be specifically detected in human sera or plasma, several control experiments were performed. These included detection of human neu in the culture supernatant of cell lines that express high levels of human neu and in the sera of nude mice bearing tumors.

Figure 11:
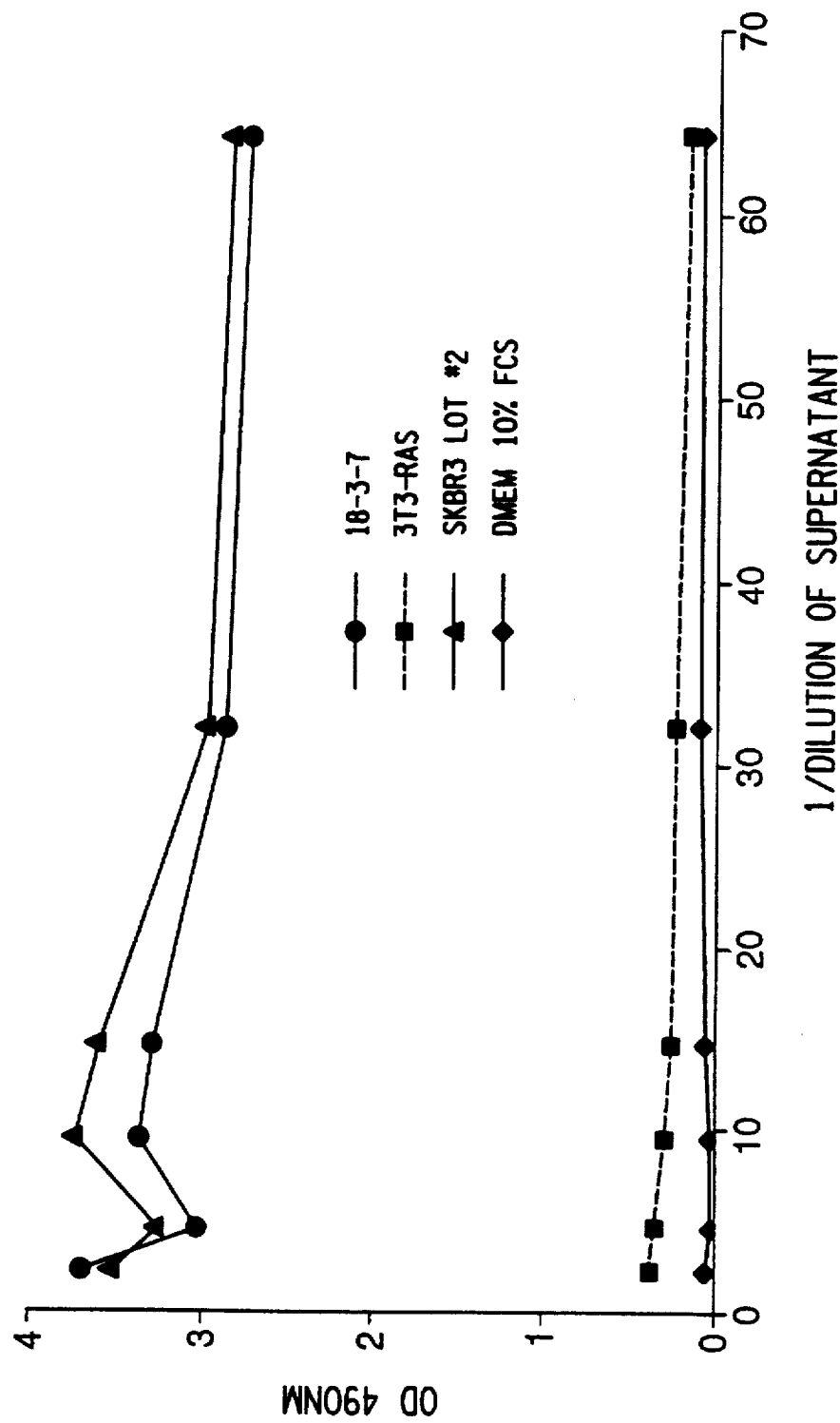
FIG. 11 shows results of a capture immunoassay of supernatant fluids from 18-3-7 cells (NIH 3T3 cells transformed with the human neu gene-and expressing the p185 protein on the cell surface), 3T3 ras cells (NIH 3T3 cells transformed with the ras gene and not expressing the human p185 protein on the cell surface), and SK-BR-3 human breast carcinoma cells and culture media-DMEM supplemented with 10% fetal calf serum. In the capture immunoassay, an anti-neu monoclonal antibody, NB-3, was used as the capture reagent and biotinylated anti-human neu monoclonal antibody, TA-1, was used as part of the detection system.
Figure 12:
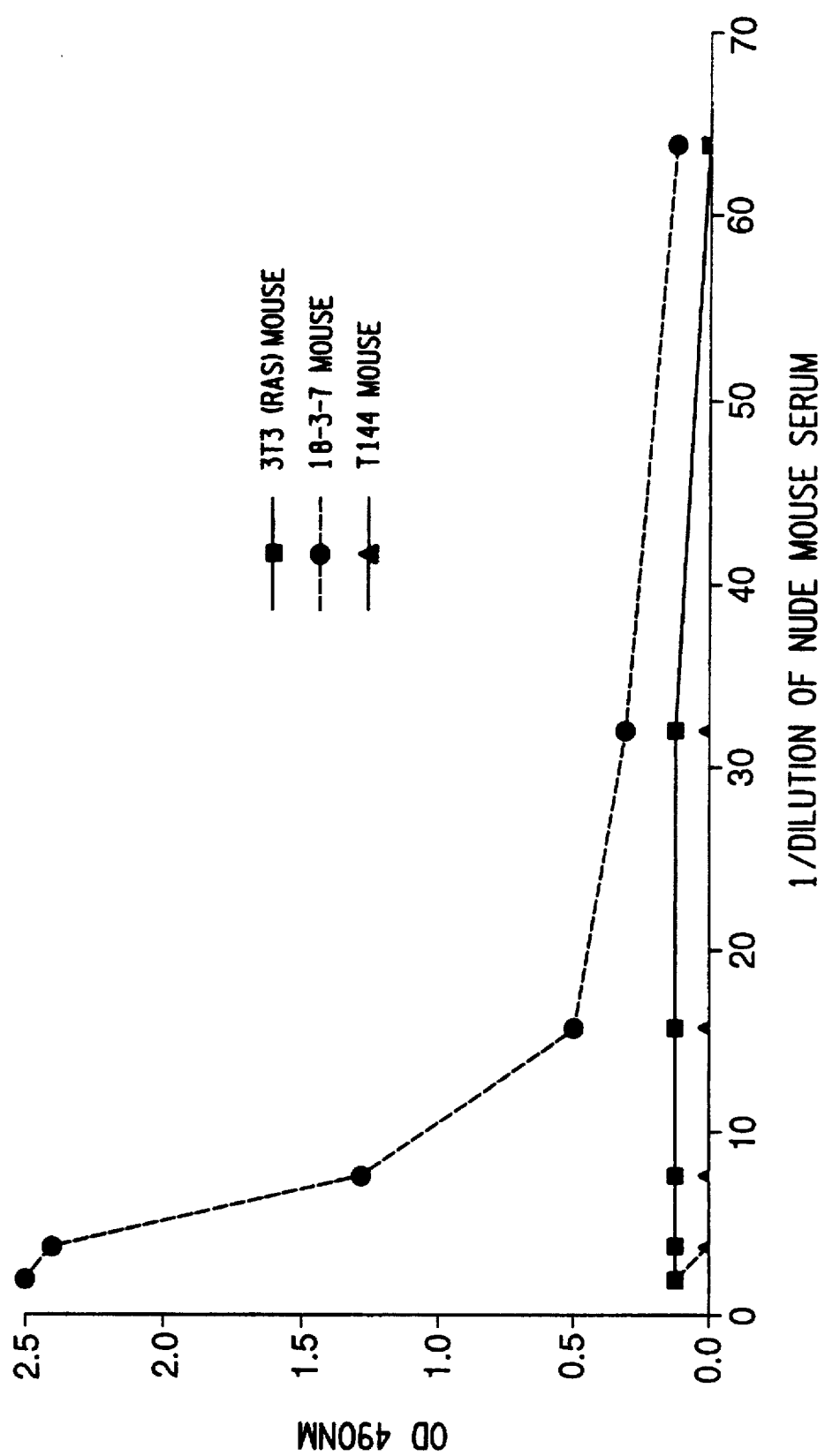
FIG. 12 shows results of a capture immunoassay using sera from mice bearing tumors derived from T144 which is a ras-transformed NIH 3T3 cell line derived from an activated ras gene obtained from breast carcinoma cell line HS0578t, sera from mice bearing tumors expressing the p185 protein (18-3-7 mouse), and sera from mice bearing tumors not expressing the p185 protein (3T3 (ras)). These sera assayed using an anti-human neu monoclonal antibody, TA-1, as the capture antibody and a biotinylated anti-human neu monoclonal antibody, BD-5, was used as part of the detection system.

FIG. 11 shows the results of a capture immunoassay of human neu from culture supernatants of cell lines using NB-3 as the capture antibody and biotinylated TA-1 as the detector antibody. The results show that a human neu related gene product can be detected in the supernatant of murine (18-3-7) or human (SK-BR-3) cell lines that express high levels of human neu but not in the supernatant of a cell line that does not express human neu, 3T3-ras, or in media alone. Two of these cell lines are able to grow as tumors in nude mice (18-3-7 and 3T3-ras). Mice bearing tumors derived from injecting these cell lines subcutaneously into nude mice were bled and their sera was analyzed for the presence of human neu by a capture immunoassay using TA-1 as the capture antibody and biotinylated BD-5 as the detector antibody. The results of this assay are shown in FIG. 12. As with the cell or tumor lysates and the cell culture supernatants, only the sera of the nude mouse bearing a tumor that expressed human neu reacted in the assay. Both normal nude mouse sera and sera from a nude mouse bearing a tumor that did not express human neu did not react in the assay.

These experiments indicated that a human neu related protein was found in the sera of nude mice bearing tumors expressing human neu as well as the cell line causing the nude mouse tumor. Human neu was found in the supernatant of human cell lines expressing neu (SK-BR-3).

Figure 13:
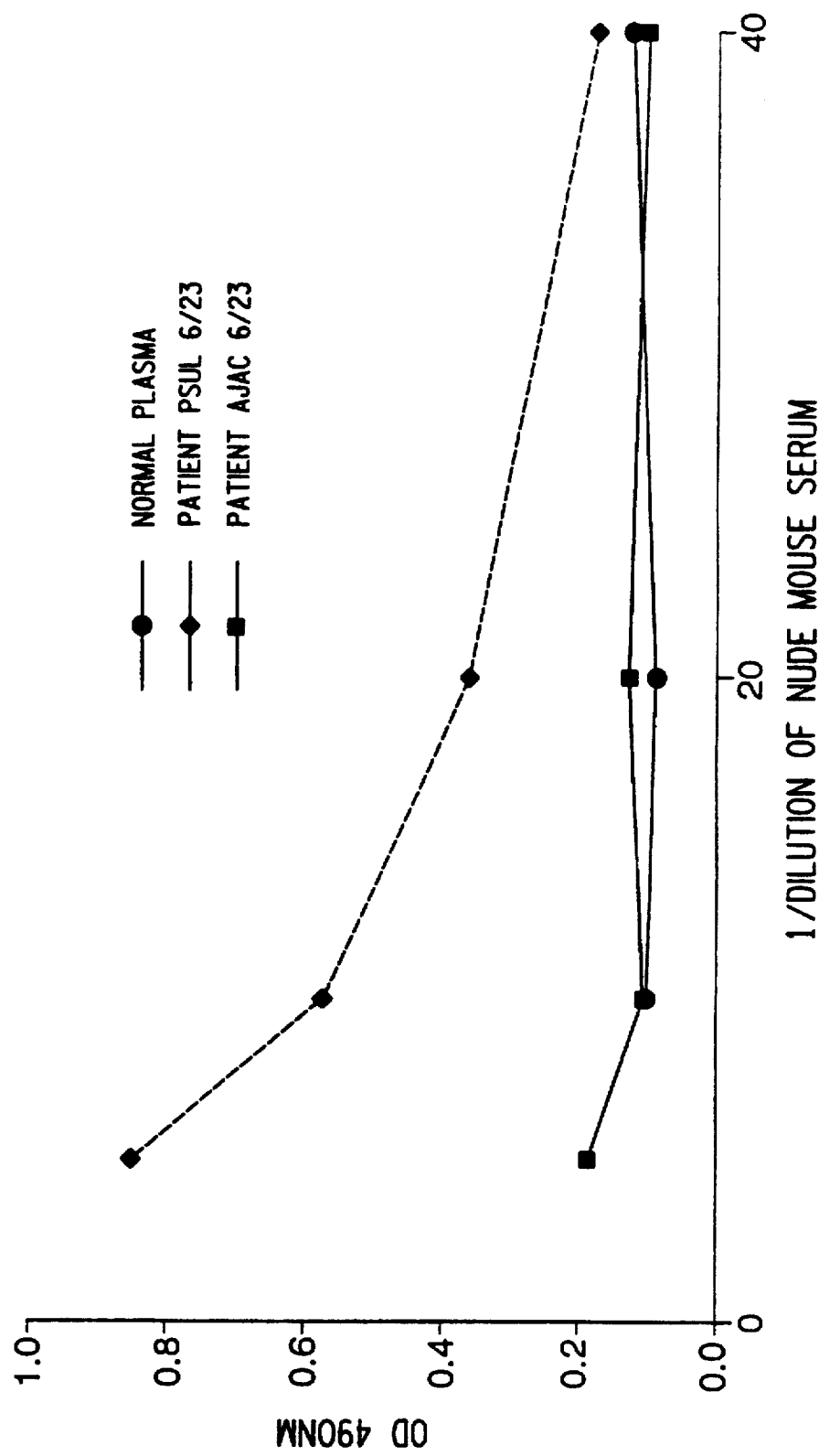
FIG. 13 shows the results of a capture immunoassay in which the anti-human neu monoclonal antibody TA-1, was used as the capture reagent and biotinylated BD-5 was used as part of the detection system. Samples for analysis included normal human plasma and plasma from two breast carcinoma patients.

Assays were performed that were designed to test the hypothesis that patients with tumors expressing high levels of human neu will have sera containing a human neu related protein. One series of assays used anti-neu Mab TA-1 as the capture reagent and biotinylated BD-5 as the detection reagent. Samples for analysis included normal human plasma and plasma from two breast carcinoma patients. Results show that normal plasma and plasma from patient AJAC were virtually unreactive in this particular assay whereas plasma from patient PSUL showed significant reactivity in this assay suggesting that a human neu related protein was present in the plasma of the breast carcinoma patient PSUL (FIG. 13).

This experiment was repeated on a larger number of patients with Mab NB-3 as the capture reagent (affixed to the solid support) and biotinylated MAB TA-1 as the detection reagent. Using this assay, about 225 separate plasma samples were evaluated for reactivity with Deu-specific monoclonal antibodies. The samples were obtained from Dr. Daniel Hayes and Dr. Don Kufe of the Dana-Farber Cancer Institute. The specimens consisted of plasma samples from normal individuals, plasma samples from individuals with benign breast disease, plasma samples from individuals with breast cancer, plasma samples from individuals with gastric carcinoma and individuals with ovarian cancer. It appears that the average human neu value for this particular study was about 600 for the normal plasma samples, i.e., plasma samples from normal individuals and individuals with normal (benign) breast disease. Table 2 presents the individual data obtained for samples. Table 3 presents additional data for about 66 plasma samples from ovarian cancer patients which were evaluated for reactivity with neu-specific monoclonal antibodies. It may be possible to convert the human neu values presented herein to fmol/ml.

TABLE 2 neu CAPTURE ELISA/HAYES PANEL #3/PLASMA SAMPLE RESULTS

| Sample | Human neu Values |
|---|---|
| 102 | 847.8 |
| 105 | 460.1 |
| 109 | 1877.8 |
| 110 | <500 |
| 112 | 1087.4 |
| 115 | 842.1 |
| 116 | 1106.5 |
| 118 | 928.6 |
| 121 | 1579.2 |
| 122 | 826.5 |
| 129 | 887.9 |
| 134 | 1133.9 |
| 136 | 1340.3 |
| 140 | 81915.0 |
| 144 | 962.2 |
| 149 | 1261.9 |
| 158 | 1363.1 |
| 165 | 7071.5 |
| 167 | 3226.5 |
| 178 | 821.8 |
| 191 | 1126.0 |
| 192 | 699.3 |
| 193 | 1076.2 |
| 204 | 7359.0 |
| 207 | 1924.8 |
| 225 | 1969.5 |
| 242 | 853.9 |
| 251 | 892.9 |
| 253 | 1091.0 |
| 264 | 815.4 |
| 266 | 919.3 |
| 278 | 776.8 |
| 280 | 979.7 |
| 281 | 391.4 |
| 274 | 61730.0 |
| 284 | 744.7 |
| 290 | 583.0 |
| 291 | 2439.3 |
| 292 | 715.9 |
| 300 | 763.6 |
| 305 | 175573.3 |
| 316 | 660.6 |
| 317 | 841.8 |
| 320 | 576.7 |
| 322 | 857.0 |
| 324 | 649.2 |
| 330 | 927.6 |
| 339 | 878.0 |
| 355 | 1128.0 |
| 356 | 662.6 |
| 360 | 859.0 |
| 370 | 677.8 |
| 376 | 3486.7 |
| 378 | 834.2 |
| 385 | 422.3 |
| 386 | 733.1 |
| 390 | 1099.0 |
| 392 | 674.0 |
| 395 | 5675.7 |
| 397 | 664.5 |

TABLE 2-continued neu CAPTURE ELISA/HAYES PANEL #3/PLASMA SAMPLE RESULTS

| Sample | Human neu Values |
|---|---|
| 398 | 1474.3 |
| 409 | 10278.7 |
| 412 | 1068.0 |
| 418 | 1142.7 |
| 420 | 1363.7 |
| 425 | 895.2 |
| 428 | 1106.0 |
| 430 | 928.6 |
| 435 | 562.6 |
| 436 | 5568.0 |
| 437 | 560.4 |
| 411 | 773.3 |
| 474 | 1049.0 |
| 510 | 558.9 |
| 517 | 865.8 |
| 521 | 2156.7 |
| 522 | 3042.0 |
| 526 | 599.5 |
| 529 | 1542.0 |
| 530 | 591.3 |
| 533 | 932.6 |
| 537 | 1174.8 |
| 542 | 582.9 |
| 556 | 645.8 |
| 560 | 845.4 |
| 583 | 8534.7 |
| 587 | 669.8 |
| 599 | 1054.0 |
| 604 | 533.0 |
| 609 | 78266.7 |
| 611 | 988.5 |
| 615 | 1065.0 |
| 619 | 839.9 |
| 621 | 1238.5 |
| 622 | 1211.5 |
| 623 | 1061.0 |
| 629 | 866.4 |
| 637 | 956.1 |
| 638 | 400.1 |
| 659 | 1493.0 |
| 662 | 1074.0 |
| 673 | 2130.3 |
| 679 | 644.3 |
| 683 | 710.5 |
| 686 | 757.5 |
| 687 | 1204.3 |
| 691 | 583.9 |
| 692 | 647.2 |
| 699 | 1010.5 |
| 702 | 1921.0 |
| 708 | 860.2 |
| 715 | 1053.0 |
| 721 | 947.1 |
| 728 | 815.9 |
| 732 | 669.3 |
| 746 | 725.3 |
| 749 | 666.1 |
| 753 | 1108.5 |
| 764 | 10905.0 |
| 130 | 548.8 |
| 141 | 1069.0 |
| 169 | 822.7 |
| 187 | 812.7 |
| 198 | 328.2 |
| 265 | 664.1 |
| 273 | 752.1 |
| 283 | 1515.5 |
| 294 | 589.2 |
| 299 | 586.3 |
| 341 | 674.2 |
| 359 | 851.6 |

TABLE 2-continued neu CAPTURE ELISA/HAYES PANEL #3/PLASMA SAMPLE RESULTS

| Sample | Human neu Values |
|---|---|
| 364 | 724.7 |
| 383 | 964.0 |
| 410 | 760.7 |
| 424 | 563.2 |
| 427 | 458.0 |
| 429 | 677.1 |
| 431 | 1267.3 |
| 489 | 423.4 |
| 511 | 443.5 |
| 520 | 1084.0 |
| 539 | 1143.0 |
| 567 | 502.4 |
| 596 | 667.9 |
| 606 | 675.4 |
| 618 | 646.8 |
| 710 | 491.8 |
| 718 | 556.6 |
| 759 | 1065.5 |
| 1303 | 4277.0 |
| 1350 | 2068.0 |
| 1552 | 804.6 |
| 1562 | 951.3 |
| 1810 | 4347.5 |
| 1944 | 1339.0 |
| 1978 | 828.3 |
| 1983 | 2694.0 |
| 2004 | 1190.5 |
| 2105 | 760.7 |
| 2236 | 279.1 |
| 2553 | 1248.5 |
| 2661 | 21668.5 |
| 2669 | 2831.5 |
| 2823 | 714.8 |
| 2892 | 1758.0 |
| 2904 | 31008.0 |
| 2934 | 7129.3 |
| 3282 | 882.4 |
| 3527 | 621.0 |
| B01 | 713.5 |
| B02 | 586.9 |
| B03 | 581.0 |
| B04 | 560.4 |
| B05 | 731.1 |
| B06 | 586.3 |
| B07 | 1038.0 |
| B08 | 1027.0 |
| B09 | 900.6 |
| B10 | 455.1 |
| B11 | 332.5 |
| B12 | 627.3 |
| B13 | 515.9 |
| B14 | 505.5 |
| B15 | 421.1 |
| B16 | 570.4 |
| B17 | 674.2 |
| B18 | 665.6 |
| B19 | 564.7 |
| B20 | 475.3 |
| B21 | 1297.0 |
| B22 | 344.1 |
| B23 | 824.2 |
| C10 | 496.0 |
| C12 | 547.8 |
| C21 | 362.9 |
| C24 | 422.1 |
| C25 | 692.0 |
| C27 | 880.6 |
| C28 | 327.8 |
| C29 | 636.5 |
| C44 | 790.0 |
| C54 | 669.8 |
| C55 | 570.0 |
| C80 | 605.1 |
| C82 | 664.3 |
| C83 | 782.2 |
| C84 | 574.5 |
| C86 | 543.6 |
| C89 | 565.9 |
| C90 | 598.5 |
| C91 | 567.7 |
| C92 | 679.2 |
| C93 | 624.3 |
| C96 | 717.0 |
| C97 | 505.9 |
| C98 | 437.2 |
| C99 | 571.1 |
| C100 | 783.9 |
| C101 | 737.6 |
| C102 | 572.8 |
| C103 | 528.2 |
| C104 | 823.4 |
| C105 | 608.8 |
| C108 | 651.8 |
| C109 | 468.1 |
| C110 | 634.6 |
| C111 | 617.4 |
| C112 | 373.7 |
| C114 | 529.9 |
| G1 | 378.0 |
| G2 | 542.8 |
| G3 | 653.1 |
| G5 | |
| G6 | 750.2 |
| G7 | 473.6 |
| G8 | 600.01 |
| LW01 | 567.7 |
| LW02 | 445.8 |
| LW03 | 586.5 |
| LW04 | 693.0 |
| LW05 | 565.9 |
| LW06 | 404.6 |
| LW07 | 754.7 |
| LW08 | 886.9 |
| LW09 | 555.6 |
| LW10 | 567.7 |
| LW11 | 454.4 |
| LW12 | 411.5 |
| LW13 | 677.5 |
| LW14 | 540.2 |
| LW15 | 611.4 |
| LW16 | 1263.0 |

TABLE 3 neu Capture ELISA Ovarian Plasmas

| Sample | Human neu Values |
|---|---|
| E01 | 938.8 |
| E02 | 495.1 |
| E03 | 794.9 |
| E04 | 1057.4 |
| E05 | 829.2 |
| E06 | 1769.8 |
| E07 | 757.1 |
| E08 | 1138.0 |
| E09 | 980.7 |

TABLE 3-continued neu Capture ELISA
Ovarian Plasmas

| Sample | Human neu Values |
|---|---|
| E011 | 917.7 |
| E012 | 697.5 |
| E016 | 748.8 |
| E017 | 807.0 |
| E019 | 632.6 |
| E020 | 729.1 |
| E021 | 491.7 |
| E022 | 549.9 |
| E023 | 946.2 |
| E024 | 516.5 |
| E025 | 550.8 |
| E026 | 1099.2 |
| E027 | 641.9 |
| E028 | 633.3 |
| E029 | 394.9 |
| E030 | 473.8 |
| E031 | 852.1 |
| E032 | 824.7 |
| E033 | 698.8 |
| E034 | 760.4 |
| E035 | 1703.0 |
| E036 | 566.7 |
| E037 | 512.2 |
| E038 | 901.4 |
| E039 | 709.9 |
| E040 | 488.8 |
| E041 | 442.3 |
| E042 | 483.8 |
| E043 | 613.1 |
| E044 | 634.6 |
| E045 | >10000 |
| E046 | 422.3 |
| E047 | 525.7 |
| E048 | 590.0 |
| E049 | 557.8 |
| E050 | 803.9 |
| E051 | 609.1 |
| E052 | 782.6 |
| E053 | 386.6 |
| E054 | 890.8 |
| E055 | 558.9 |
| E056 | >10000 |
| E057 | 595.6 |
| E058 | 923.5 |
| E059 | 983.9 |
| E060 | 760.3 |
| E061 | 489.0 |
| E062 | 485.6 |
| E063 | 574.4 |
| E064 | 739.1 |
| E065 | 522.3 |
| E066 | 667.5 |
| E067 | 445.0 |
| E068 | 582.5 |
| E069 | 604.7 |
| E070 | 792.6 |
| E071 | 1817.5 |

D. Immunoblot Evaluation of Plasmas

Figure 15:
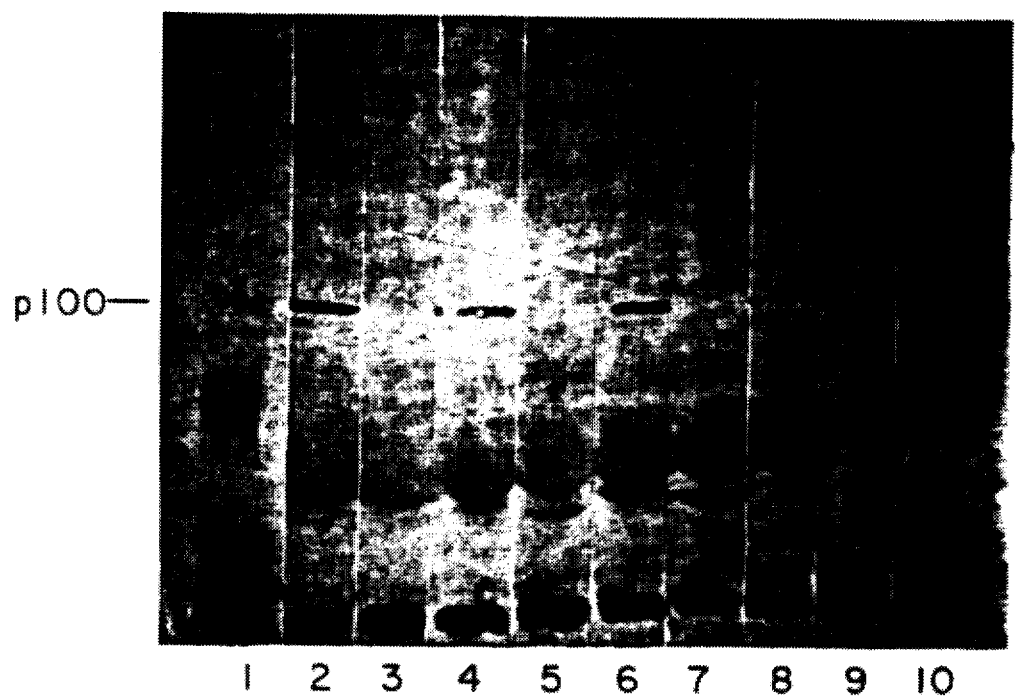
FIGS. 15, 16, 17 and 18 present immunoblot results showing detection of p100 in human plasma samples obtained from breast, gastric, and ovarian carcinoma patients.
Figure 16:
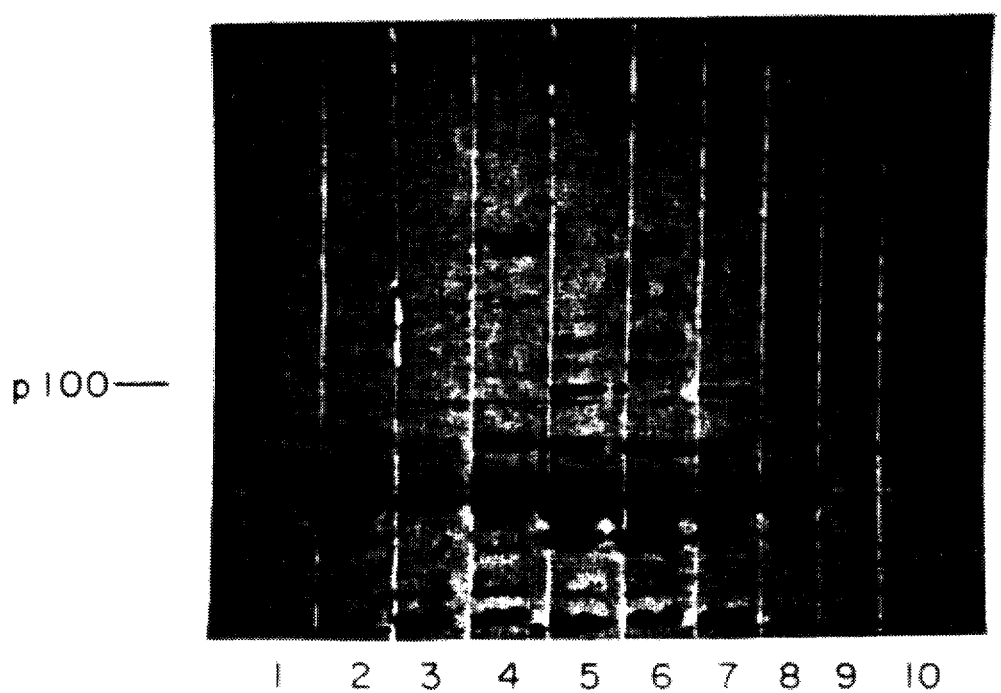
Figure 17:
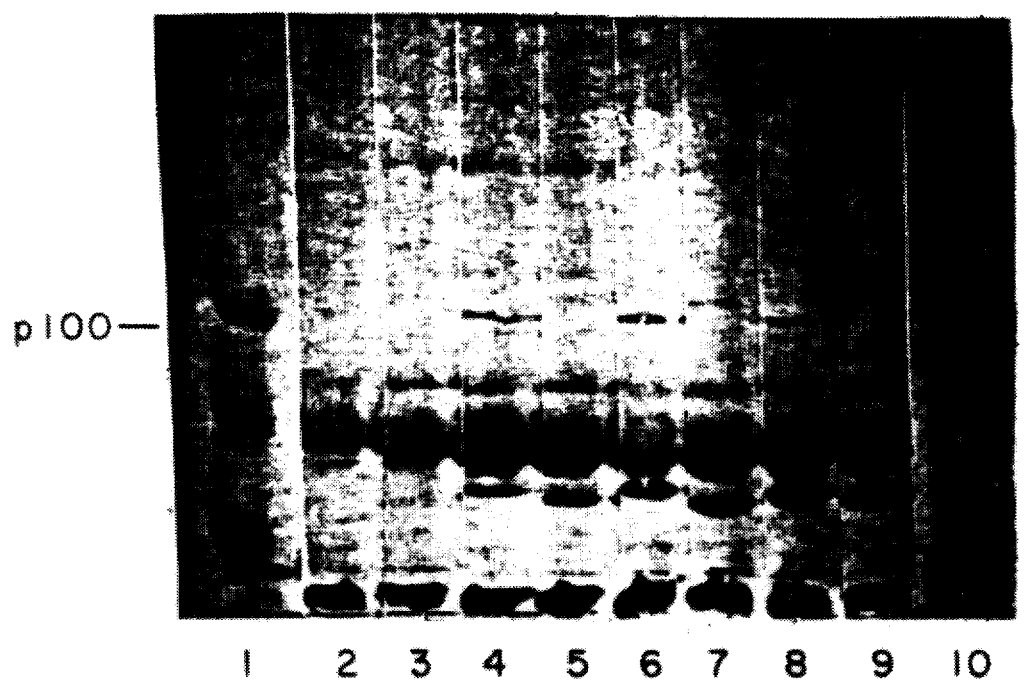

Some of the samples which were evaluated by the ELISA protocol as described above were evaluated by immunoblot as described below using the anti-human neu related monoclonal antibody designated OD-3. Immunoblot results presented in FIGS. 15-17 are set forth in Table 4 along with corresponding human neu values as determined by the human neu ELISA.

The immunoblot procedure entailed the following protocol:

Approximately 10 µl of the plasma samples were precleared with rabbit anti-mouse protein A agarose for 30 minutes at 4° C. using a rotating wheel or rocker. The sample was centrifuged in an eppendorf centrifuge. The supernatant was decanted and saved. About 50 µl of sodium dodecyl sulfate reducing buffer with methyl green (sample loading buffer, SLB) was added to each sample. 50 µl of SLB was added to the high molecular weight standard. The samples were then heated in a hot oil bath for five minutes at 100° C.

The samples were electrophoresed on a 1.5 mm or 3.0 mm thick 5% SDS-polyacrylamide gels, using a 3.0% stacking gel. The separated proteins were transferred onto nitrocellulose using the BioRad Transblot apparatus. The nitrocellulose filter was then blocked for one hour in Blotto (3% dry milk, 2% normal goat serum, 0.1% Tween-20 in PBS) and incubated for 3 hours at room temperature with about 10 µg/ml of OD3 or a class matched control diluted to 10 µg/ml in 50 ml Blotto. Filters were rinsed 3 times in a high salt wash buffer (20 mM Tris-HCl, 1M NaCl, 0.05% Tween-20, pH 7.5) and were then incubated with alkaline phosphatase labeled goat anti-mouse IgM (Kirkegaard & Perry Labs) for at least one hour at room temperature. They were washed again 3 times with the high salt wash buffer, and the bands were visualized using a BCIP NBT substrate kit (Kirkegaard & Perry Labs).

FIG. 15 (N10) shows that OD3 detected a human neu related protein in human plasma, obtained from a lactating woman, an individual having benign breast disease and a breast carcinoma patient, having an approximate molecular weight of about 100,000 daltons in lanes 2, 4, 6, and 8. No such protein (p100) was detected in lanes 3, 5, 6, and 9. Lane 1 contained molecular weight markers. Lanes 2 and 3 contained plasma from a lactating woman. Lanes 4 and 5 contained controls. Lanes 6 and 7 contained plasma from breast carcinoma patient #109. (Plasma taken from patient #109 had a human neu value of 1,877.8 as determined by ELISA.) Lanes 8 and 9 contained plasma from breast carcinoma patient #283. (Plasma taken from patient #283 had a human neu value of 1,515.5 as determined by ELISA.) Lanes 2, 4, 6 and 8 were blotted with monoclonal antibody OD3. Lanes 3, 5, 7 and 9 were blotted with the class matched negative control monoclonal antibody, TEPC 183 (a myeloma IgM purchased from Litton Bionetics).

FIG. 16 (N12) shows that OD3 detected a neu related protein in human plasma, obtained from an individual having benign breast disease and from a breast carcinoma patient, having an approximate molecular weight of about 100,000 daltons in lanes 1, 5, and 7. No such band was detected in lanes 2, 3, 4, 6, and 8. Lanes 1 and 2 contained plasma from an individual with benign breast disease. Lanes 3 and 4 contained plasma from an individual with gastric cancer. Lanes 5 and 6 contained plasma from breast carcinoma patient #2661. (Plasma taken from patient #2661 had a human neu value of 21,668.5 as determined by ELISA.) Lanes 7 and 8 contained plasma from breast carcinoma patient #2904. (Plasma taken from patient #2904 had a human neu value of 31,008.0 as determined by ELISA.) Lane 10 contained molecular weight markers. Lanes 1, 3, 5, and 7 were blotted with monoclonal antibody OD3. Lanes 2, 4, 6, and 8 were blotted with the negative control antibody TEPC 183.

FIG. 17 (N13) shows that OD3 detected a human neu related protein in human plasma, obtained from an individual with benign breast disease and a breast carcinoma patient, having an approximate molecular weight of about 100,000 daltons in lanes 4, 6 and 8. No such band was detected in lanes 2, 3, 5, 7, and 9. Lane 1 contained molecular weight markers. Lanes 2 and 3 contained plasma from an individual with gastric carcinoma. Lanes 4 and 5 contained plasma from an individual with benign breast disease. Lanes 6 and 7 contained plasma from an breast carcinoma patient #140. (Plasma taken from patient #140 had a human neu value of 81,915.0 as determined by ELISA.) Lanes 8 and 9 contained plasma from breast carcinoma patient #305. (Plasma taken from patient #305 had a human neu value of 175573.3 as determined by ELISA.) Lanes 2, 4, 6, and 8 were blotted with anti-human neumonoclonal antibody OD3. Lanes 3, 5, 7, and 9 were blotted with the negative control monoclonal antibody TEPC 183.

Figure 18:
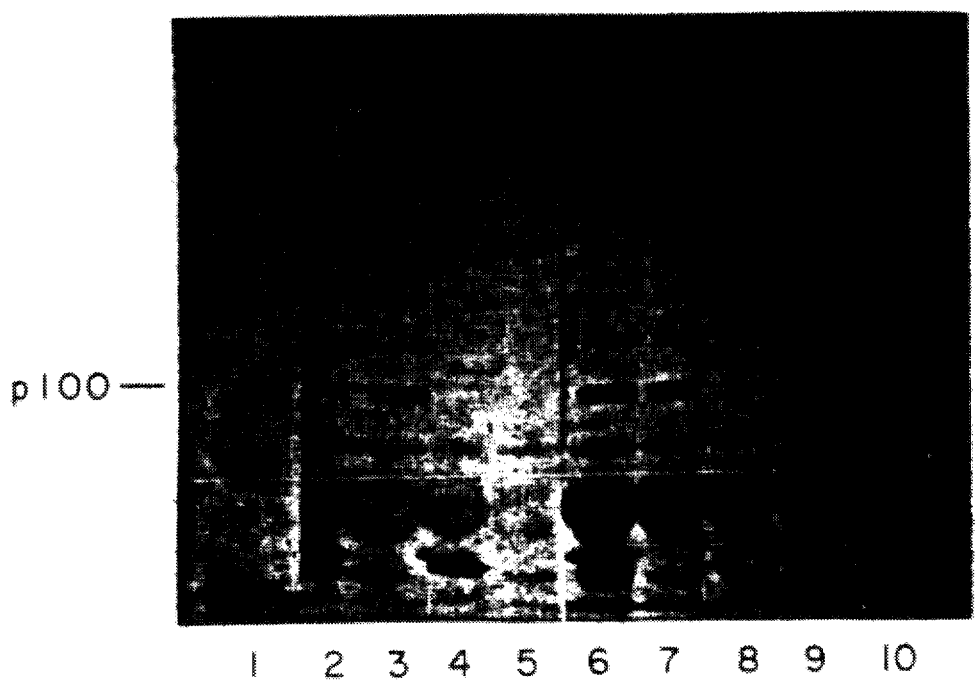

FIG. 18 (NBS) shows that OD3 detected a human neu related protein in human plasma obtained from an individual with ovarian carcinoma having an approximate molecular weight of about 100,000 daltons in lanes 2, 3, 6, and 7. No such band was detected in lanes 4, 5, 8, 9, and 10. Lanes 2, 4, 6, and 8 contained plasma from ovarian cancer patient #45. (Plasma taken from patient #45 had a human neu value of 10,000 as determined by ELISA.) Lanes 3, 5, 7, and 8 contained plasma from ovarian cancer patient #35. (Plasma taken from patient #35 had a human neu value of 1,703 as determined by ELISA.) Lane 10 did not contain a plasma sample. Rather, it contained the control which was tumor extract electrophoresed from a cell line, 17-7-8 known to contain human neu p185. Lanes 2 and 3 were blotted with anti-human neu monoclonal antibody OD3 for one hour. Lanes 4 and 5 were blotted with the negative control monoclonal antibody TEPC 183 for one hour. Lanes 6 and 7 were blotted with anti-human neu monoclonal antibody OD3 for three hours. Lanes 8 and 9 were blotted with the negative control antibody TEPC 183 for three hours. Lane 10 was blotted with OD3 which detected the human neu related gene product p185 in the tumor extract.

TABLE 4

| Plasma Sample (patient #) | Human neu ELISA Results (human neu values) | Immunoblot Results | |
|---|---|---|---|
| | | p185 | p100 |
| 109 | 11871.8 | − | + |
| 283 | 2,515.5 | − | + |
| 2661 | 21,668.5 | − | + |
| 2904 | 31,008.0 | − | + |
| 140 | 81,915.0 | − | + |
| 305 | 175,573.3 | − | + |

What is claimed is:

1. An immunoassay for detecting the overexpression of human neu gene encoded p185 protein in a sample of cells comprising:
   (a) obtaining a lysate of the sample of cells;
   (b) contacting the lysate with an antibody specific for the extracellular domain of the human neu gene encoded p185 protein under conditions suitable for binding; and
   (c) comparing the level of binding with the level of binding in a lysate of normal cells, wherein a higher level of binding is indicative of the overexpression of the human neu gene encoded p185 protein in the sample of cells.

2. The immunoassay of claim 1, wherein the sample of cells is from human breast tissue.

3. The immunoassay of claim 1, wherein the sample of cells is from preneoplastic tissue.

4. The immunoassay of claim 1, wherein the sample of cells is from neoplastic tissue.

5. The immunoassay of claim 1, wherein the antibody in step (b) is a monoclonal antibody.

6. The immunoassay of claim 1, wherein the antibody in step (b) is a polyclonal antibody.

7. An immunoassay for human neu gene encoded p185 protein in a cell lysate comprising:
   (a) contacting a sample of the cell lysate with a first antibody that is specific for an epitope of the extracellular domain of the human neu gene encoded p185 protein to form a first antibody-p185 protein complex;

(b) contacting the first antibody-p185 protein complex with a second antibody that is specific for a different epitope of the human neu gene encoded p185 protein to form a first antibody-p185 protein-second antibody complex; and (c) detecting the amount of the first antibody-p185 protein-second antibody complex, wherein the amount of the first antibody-p185 protein-second antibody complex is indicative of the quantity of human neu gene encoded p185 protein in the sample.

8. The immunoassay of claim 7, wherein the cell lysate is a lysate of cells from normal tissue.

9. The immunoassay of claim 7, wherein the cell lysate is a lysate of cells from preneoplastic tissue.

10. The immunoassay of claim 7, wherein the cell lysate is a lysate of cells from neoplastic tissue.

11. The immunoassay of claim 7, wherein the first antibody is a monoclonal antibody.

12. The immunoassay of claim 7, wherein the first antibody is a polyclonal antibody.

13. The immunoassay of claim 11, wherein the second antibody is a polyclonal antibody.

14. The immunoassay of claim 12, wherein the second antibody is a monoclonal antibody.

15. The immunoassay of claim 11, wherein the monoclonal antibody is selected from the group consisting of TA-1, NB-3, OD3, and BD5-2d.

16. The immunoassay of claim 14, wherein the monoclonal antibody is selected from the group consisting of TA-1, NB-3, OD3, and BD5-2d.

17. The immunoassay of claim 7, wherein the second antibody is detected by contacting it with a labeled third antibody.

18. The immunoassay of claim 17, wherein the label is horseradish peroxidase.

19. The immunoassay of claim 17, wherein the label is alkaline phosphatase.

20. The immunoassay of claim 19, wherein the alkaline phosphatase label is detected by reaction with a chemiluminescent substrate.

21. The immunoassay of claim 11, wherein the second antibody is a monoclonal antibody.

22. The immunoassay of claim 21, wherein the monoclonal antibody is selected from the group consisting of TA-1, NB-3, OD3, and BD5-2d.

23. An immunoassay for,-human neu gene encoded p185 protein in a cell lysate comprising:

(a) contacting a sample of the cell lysate with a first antibody that is bound to a solid support and is specific for an epitope of the extracellular domain of the human neu gene encoded p185 protein to form a first antibody-p185 protein complex;

(b) contacting the first antibody-p185 protein complex with a second antibody that is specific for a different epitope of the human neu gene encoded p185 protein to form a first antibody-p185 protein-second antibody complex; and (c) detecting the amount of the first antibody-p185 protein-second antibody complex, wherein the amount of the first antibody-p185 protein-second antibody complex is indicative of the quantity of human neu gene encoded p185 protein in the sample.

24. The immunoassay of claim 23, wherein the cell lysate is a lysate of cells from normal tissue.

25. The immunoassay of claim 23, wherein the cell lysate is a lysate of cells from preneoplastic tissue.

26. The immunoassay of claim 23, wherein the cell lysate is a lysate of cells from neoplastic tissue.

27. The immunoassay of claim 23, wherein the first antibody is a monoclonal antibody.

28. The immunoassay of claim 23, wherein the first antibody is a polyclonal antibody.

29. The immunoassay of claim 27, wherein the second antibody is a polyclonal antibody.

30. The immunoassay of claim 28, wherein the second antibody is a monoclonal antibody.

31. The immununoassay of claim 27, wherein the monoclonal antibody is selected from the group consisting of TA-1, NB-3, OD3, and BD5-2d.

32. The immunoassay of claim 30, wherein the monoclonal antibody is selected from the group consisting of TA-1, NB-3, OD3, and BD5-2d.

33. The immunoassay of claim 23, wherein the second antibody is detected by contacting it with a labeled third antibody.

34. The immunoassay of claim 33, wherein the label is horseradish peroxidase.

35. The immunoassay of claim 33, wherein the label is alkaline phosphatase.

36. The immunoassay of claim 35, wherein the alkaline phosphatase label is detected by reaction with a chemiluminescent substrate.

37. The immunoassay of claim 27, wherein the second antibody is a monoclonal antibody.

38. The immunoassay of claim 37, wherein the monoclonal antibody is selected from the group consisting of TA-1, NB-3, OD3, and BD5-2d.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: Peptide ( i i i ) HYPOTHETICAL: N ( i v ) ANTI-SENSE: N ( v ) FRAGMENT TYPE: N-terminal ( x i ) SEQUENCE DESCRIPTION: SEQ ID NO:1:

```
Gly Thr Pro Thr Ala Glu Asn Pro Glu Tyr Leu Gly Leu Asp Val Pro
1               5                   10                  15
Val
```